United States Patent
Kuo et al.

(10) Patent No.: US 7,618,772 B2
(45) Date of Patent: Nov. 17, 2009

(54) METHODS AND COMPOSITIONS FOR DIAGNOSING AND SUPPRESSING METASTASIS THEREOF

(75) Inventors: Min-Liang Kuo, Taipei (TW); Cheng-Chi Chang, Taipei (TW)

(73) Assignee: National Taiwan University (TW)

( * ) Notice: Subject to any disclaimer, the term of this patent is extended or adjusted under 35 U.S.C. 154(b) by 354 days.

(21) Appl. No.: 11/689,286

(22) Filed: Mar. 21, 2007

(65) Prior Publication Data

US 2007/0172876 A1     Jul. 26, 2007

Related U.S. Application Data

(62) Division of application No. 10/871,407, filed on Jun. 18, 2004, now Pat. No. 7,214,480.

(30) Foreign Application Priority Data

Jan. 6, 2004     (TW)     ................................ 9310028 A

(51) Int. Cl.
  *C12Q 1/00*     (2006.01)
  *C12Q 1/68*     (2006.01)
  *G01N 33/574*   (2006.01)
  *G01N 33/53*    (2006.01)

(52) U.S. Cl. ................................ 435/4; 435/6; 435/7.1; 435/7.23

(58) Field of Classification Search ....................... None
See application file for complete search history.

(56) References Cited

OTHER PUBLICATIONS

Hashimoto et al , J Exp Med, vol. 187 p. 289-96, 1998.*

* cited by examiner

*Primary Examiner*—Larry R. Helms
*Assistant Examiner*—Lei Yao
(74) *Attorney, Agent, or Firm*—WPAT, P.C.; Anthony King; Kay Yang

(57) ABSTRACT

Disclosed is a method for determining metastatic potential of tumors, a method and a composition for treating/suppressing metastasis of cancers, as well as a method for obtaining a metastasis suppressor. A particular aspect of the invention relates to a method and a composition of evaluating expression levels of connective tissue growth factor (CTGF, also known as CCN2) to determine the status of tumor invasion. Another aspect of the invention relates to a method and a composition comprising a tumor suppressor, which maintains or increases an expression level of CTGF to suppress the invasion ability of tumor cells effectively. In another aspect of the invention relates to methods for obtaining a metastasis suppressor by evaluating the expression levels of CTGF after contacting suppressor candidates with a tumor cell line system.

12 Claims, 14 Drawing Sheets

A

CL1-5/neo

CL1-5/CTGF-M

A549/neo

A549/CTGF-M

B

CL1-5 / neo

CL1-5 / CTGF-M

METHODS AND COMPOSITIONS FOR DIAGNOSING AND SUPPRESSING METASTASIS THEREOF

CROSS-REFERENCE TO RELATED APPLICATIONS

This application is a Divisional of U.S. patent application Ser. No. 10/871,407, filed on Jun. 18, 2004, now allowed, which claims priority from Taiwanese Patent Application No. 093100208, filed on Jan. 6, 2004, all of which are hereby incorporated by reference in their entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of all of the prior art of record and any search that the Office deems appropriate.

BACKGROUND OF THE INVENTION

1. Field of the Invention

The present invention relates to a method and composition for diagnosing and suppressing metastasis thereof. A particular aspect of the invention relates to a method and composition of evaluating expression levels of connective tissue growth factor (CTGF, also known as CCN2) to determine the status of tumor invasion. Another aspect of the invention relates to a method and composition comprising a tumor suppressor, which maintains or increases an expression level of CTGF to suppress the invasion ability of tumor cells effectively.

2. The Prior Arts

Cancer is a leading cause of death in most developed countries. Although many researchers focus their efforts on developing effective methods to treat cancers, the difficulty of treating metastatic cancers is still a problem.

Metastasis is a process that the cancer cells spread from their original site to other areas in the body. Tumor metastasis involves detachment of tumor cells from the primary tumor mass, microinvasion of tumor cells into stromal tissue, intravasation of tumor cells into blood vessels, extravasation and growth of tumor cells in secondary sites. Many approaches have been developed to study the metastatic process in molecular levels, but the mechanisms of metastasis are still not very clear.

Occurrence of metastasis may bring high risk and death rate to patients. To optimize the prognosis, some aggressive methods with severe side-effects are taken to treat or suppress the tumor metastasis. Also, early detection of primary, metastatic, and recurrent disease can significantly impact the prognosis of patients suffering from cancers. Accordingly, determination of metastatic potential of tumor cells is very important to take adequate treatments to patients. Furthermore, there is a great need for methods which are effective to treat or suppress the tumor metastasis.

SUMMARY OF THE INVENTION

The primary object of the present invention is to provide a method for determining metastatic potential of tumor cells. Especially, the method relates to evaluating expression levels of CTGF encoded by SEQ ID NO: 1, which levels are inversely associated with tumor metastasis, to determine a metastatic potential of tumor cells. A particular aspect of the invention relates to determining levels of CTGF or mRNA encoding CTGF in cells of a biopsy sample to determine metastatic potential of lung or colorectal tumors. Another aspect of the invention relates to determining levels of CT module (SEQ ID NO: 2) in a nucleotide encoding CTGF or mRNA of the CT module in cells of a sample to determine cell invasive capacity of lung or colorectal tumors.

The secondary object of the present invention is to provide a composition for treating or suppressing metastatic tumors, especially lung or colorectal tumors. In one aspect of the invention, a composition is provided, comprising a tumor suppressor, which maintains or increases the expression levels of CTGF to effectively suppress the invasion ability of tumor cells. Particularly, the invention relates to a composition comprising an effective amount of CTGF or a nucleotide sequence encoding CTGF for treating or suppressing metastatic tumors.

Another object of the present invention is to provide a method for treating or suppressing metastatic tumors, especially for suppressing metastatic lung or colorectal tumors. A particular aspect of the invention relates to a method for treating or suppressing metastatic tumors by administrating a pharmaceutical composition in an effective amount to an individual suffering from a cancer, which composition comprises a tumor suppressor that maintains or increases an expression level of CTGF to suppress the invasion ability of tumor cells effectively. Especially, in this regard, the invention relates to a method using CTGF or a nucleotide sequence encoding CTGF to treat or suppress metastasis of lung or colorectal tumors. Further, this aspect of the invention may be accomplished by genetic therapy.

A further object of the present invention is to provide a method for obtaining a metastasis suppressor to elevate expression levels of CTGF. This aspect of the invention particularly relates to screening out and obtaining a metastasis suppressor by evaluating the ability of elevating expression levels of CTGF.

In some embodiments of the invention, tissue and fluid samples may be examined to evaluate expression levels of CTGF to determine the metastatic potential of the cells in the samples. Conventional methods such as immunoassays, ELISA assays, Western blots or immunohistochemistry may be performed to evaluate CTGF levels in samples. Alternatively, levels of mRNA encoding CTGF may be determined to evaluate the expression levels of CTGF. The mRNA encoding CTGF or cDNA generated therefrom can be determined using methods such as PCR amplification.

In accordance with one object of the invention, a composition for treating or suppressing metastatic tumors, comprises a suppressor that maintains or increases the expression levels of CTGF to effectively suppress the invasion ability of tumor cells. Preferably, CTGF or a nucleotide sequence encoding CTGF is used as the tumor suppressor in the composition. In some embodiments, the composition may comprise other types of active ingredients or pharmaceutically acceptable carrier in combination with the suppressor.

In accordance with another object of the invention, a method for treating or suppressing metastatic tumors comprises the steps of administrating a pharmaceutical composition to an individual suffering from a cancer, which composition comprises an effective amount of tumor suppressor maintaining or increasing the expression levels of CTGF, thereby effectively suppressing the tumor metastasis. In a preferred embodiment, the tumor suppressor is CTGF or a nucleotide sequence encoding CTGF.

In accordance with another object of the invention, a method for obtaining a metastasis suppressor by elevating expression levels of CTGF comprises the steps of (1) providing a system with a tumor cell line; (2) contacting a tumor suppressor candidate with the system; (3) evaluating the expression levels of CTGF in the tumor cells; and (4) screening out the tumor suppressors that elevates expression levels of CTGF in tumor cells. Preferably, the tumor cell line is selected from a group consisting of lung and colorectal cancer cell lines. More preferably, the tumor cell line is selected from lung or colorectal cancer cell lines with high invasiveness.

Having been briefly described, the present invention will be further explained with examples and figures illustrating its practice set forth below. These examples and figures should not, however, be considered to limit the scope of the invention, which is defined by the appended claims.

BRIEF DESCRIPTION OF THE DRAWINGS

The related figures in connection with the detailed description of the present invention to be made later are described briefly as follows, in which.

DETAILED DESCRIPTION OF THE PREFERRED EMBODIMENT

EXAMPLE 1

Figure 1:
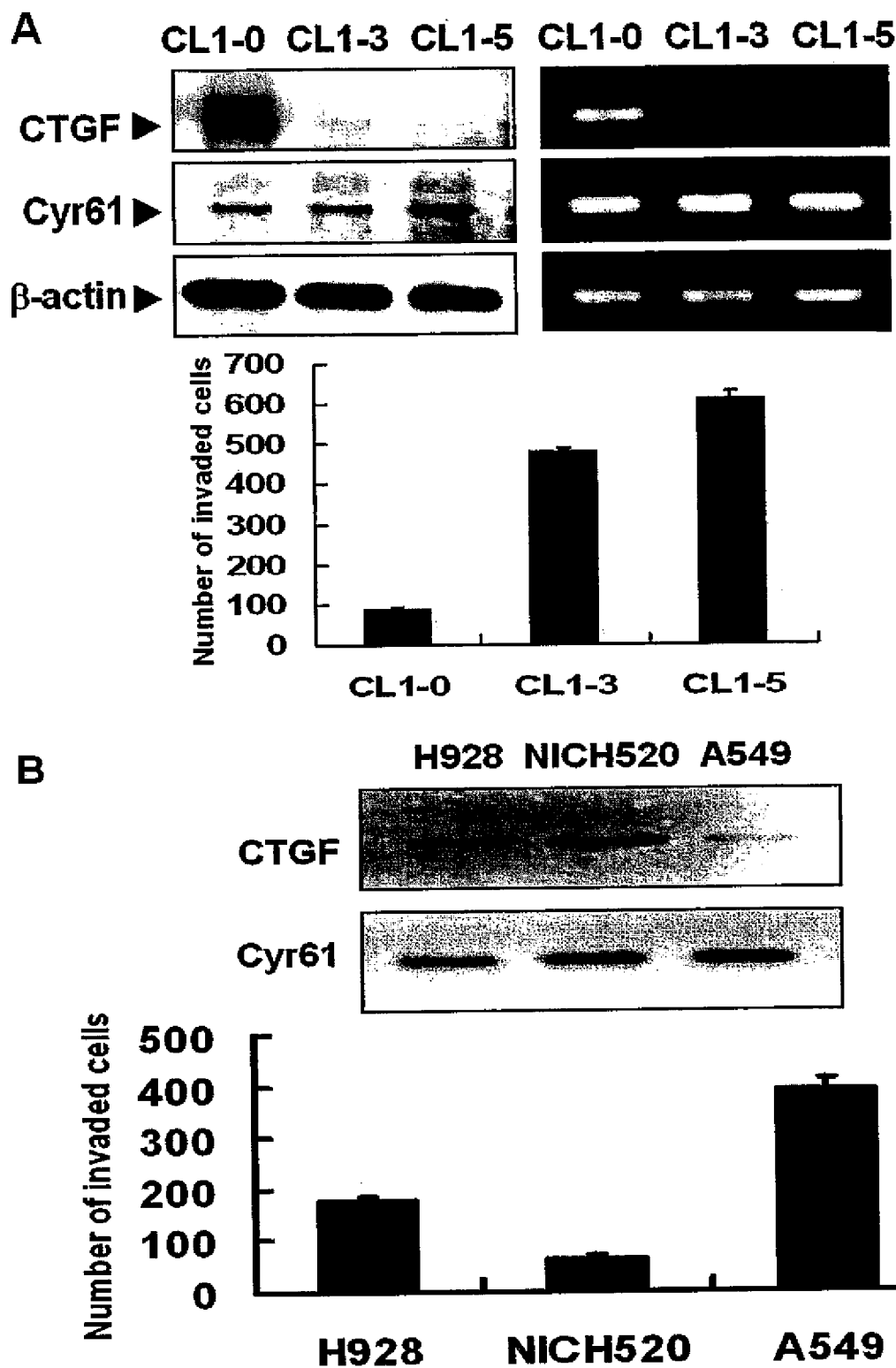
FIG. 1 shows expression of CTGF and in vitro invasion ability in human lung cancer cell lines. A (Upper left panel): Western blot analysis of the expression of CTGF and cysteine-rich 61(Cyr61) proteins. Total proteins are extracted from CL1-0, CL1-3, and CL1-5 cells and probed with polyclonal antibody specific for CTGF or Cyr61. Each lane contains 40 μg of total protein. β-Actin is used as an internal loading control. A (Upper right panel): Reverse transcription-polymerase chain reaction analysis (RT-PCR) for CTGF and Cyr61 mRNAs. A β-actin probe is used as an internal control for RNA quantity. A (Lower): The invasion activity of each clone is measured in vitro with the Boyden chamber after 48 hours. Each cell subline is assayed in three experiments carried out in triplicate. Error bars correspond to 95% confidence intervals. B (Upper): Western blot analysis of CTGF and Cry61 proteins in these human lung adenocarcinoma cancer cell lines H928, NICH520, and A549. B (Lower): In vitro invasion activity of human lung adenocarcinoma cancer cell lines is measured with the Boyden chamber after 48 hours. These experiments are repeated four times. Data are the mean; error bars show the corresponding upper 95% confidence interval.

Expression of CTGF and Invasiveness of Human Lung Adenocarcinoma Cancer Cell Lines To explore the role of CTGF in invasiveness of lung adenocarcinoma cells, expression of CTGF and the invasion ability in a panel of cell lines, CL1-0, CL1-3, CL1-5, A549, H928, and NICH520 are examined.

Cell Culture: Lung adenocarcinoma cells are grown in RPMI 1640 medium (Life Technologies, Inc. [GIBCO BRL], Rockville, Md.) with 10% fetal bovine serum (Life Technologies, Inc.) and 2 mM L-glutamine (Life Technologies, Inc.) at 37° C. in a humidified atmosphere of 5% $CO_2$ and 95% air. Lung adenocarcinoma cell lines CL1-3 and CL1-5 are sublines that are selected from parental CL1-0 cultures with a Matrigel-coated polycarbonate membrane (Collaborative Biomedical, Becton Dickinson Labware, Bedford, Mass.) in a Transwell invasion chamber as described previously (Chu, Yi-Wen et al., Am. J. Respir. Cell Mol. Biol. 1997; 17:353-60). Other lung adenocarcinoma cell lines used, A549, H928, and NICH520, are obtained from the American Type Culture Collection (Manassas, Va.). Adherent cells are detached from the culture dishes with trypsin/EDTA (Sigma, Deisenhofen, Germany).

Western Blotting: Cells are washed with phosphate-buffered saline (PBS) containing 5 mM EDTA and 1 mM sodium orthovanadate, and then scraped into lysis buffer (20 mM Tris-HCl [pH 8.0], 137 mM NaCl, 10% glycerol, 2 mM EDTA, 1 mM phenylmethylsulfonyl fluoride, 20 µM leupeptin, and 0.15 U/mL aprotinin) and stored for 30 minutes on ice. The lysed cells are centrifuged at 14,500 g for 30 minutes at 4° C., and the supernatant is collected. Proteins in the supernatant are quantified by spectrophotometry. Proteins in the total cell lysate (40 µg of protein) are separated by sodium dodecyl sulfate-polyacrylamide gel electrophoresis in 10-12% gels and electrotransferred to a polyvinylidene difluoride membrane (Immobilon-P membrane; Millipore Corp., Bedford, Mass.). After the blot is blocked in a solution of 5% skim milk, 0.1% Tween 20, and PBS, membrane-bound proteins are probed with primary antibodies against CTGF, CYR61, β-actin. The membrane is washed and then incubated with horseradish peroxidase-conjugated secondary antibodies for 30 minutes. Antibody-bound protein bands are detected with enhanced chemiluminescence reagents (Amersham Pharmacia Biotech) and photographed with Kodak X-Omat Blue autoradiography film.

Reverse Transcription-Polymerase Chain Reaction (RT-PCR): Reverse transcription (RT) of RNA isolated from cells is performed in a final reaction volume of 20 µL containing 5 µg of total RNA in Moloney murine leukemia virus reverse transcriptase (MMLV) buffer (Promega, Madison, Wis., USA), which consists of 10 mM dithiothreitol, all four deoxynucleoside 5'-triphosphates (dNTPs; each at 2.5 mM), 1 µg of $(dT)_{12-18}$ primer, and 200 units of MMLV reverse transcriptase (Promega, Madison, Wis., USA). The reaction mixture is incubated at 37° C. for 2 hours, and the reaction is terminated by heating at 70° C. for 10 minutes. One microliter of the reaction mixture is then amplified by polymerase chain reaction (PCR) with the following primers: CTGF primer (SEQ ID NO: 3), to produce a 500-base-pair (bp) fragment of the CTGF gene; Cyr61 primer (SEQ ID NO: 4), to produce a 450-bp fragment of the Cyr61 gene; and β-actin primer (SEQ ID NO: 5), to produce a 320-bp fragment product of the β-actin gene, use as the internal control. The PCR amplification is carried out in a reaction buffer containing 20 mM Tris-HCl (pH 8.4), 50 mM KCl, 1.5 mM $MgCl_2$, all four dNTPs (each at 167 μM), 2.5 units of Taq DNA polymerase, and 0.1 μM primers. The reactions are performed in a Biometra Thermoblock (Biometra Inc. Florida, USA) with the following program: denaturing for 1 minute at 95° C., annealing for 1 minute at 58° C., and elongating for 1 minute at 72° C. for a total of 23 cycles; the final extension takes place at 72° C. for 10 minute. Equal volumes of each PCR sample are subjected to electrophoresis in a 1% agarose gel, which is then stained with ethidium bromide and photographed under UV illumination.

Boyden Chamber Assay: For invasion assays, modified Boyden chambers are used with filter inserts (pore size, 8 μm) coated with Matrigel (40 μg; Collaborative Biomedical, Becton Dickinson Labware) in 24-well dishes (Nucleopore Corp., Pleasanton, Calif.). Approximately $2.5 \times 10^4$ to $1 \times 10^6$ cells in 100 μL of complete RPMI 1640 medium are placed in the upper chamber, and 1 mL of the same medium is placed in the lower chamber. After 48 hours in culture, cells are fixed in methanol for 15 minutes and then stained with 0.05% crystal violet in PBS for 15 minutes. Cells on the upper side of the filters are removed with cotton-tipped swabs, and the filters are washed with PBS. Cells on the underside of the filters are viewed and counted under a Leica Microsystems (Type: 090-135.001). Each clone is plated in triplicate in each experiment, and each experiment is repeated for at least three times.

Statistical Analysis: Statistical evaluation of the data is performed with a two-tailed Student's t test for simple comparison between two values when appropriate. All statistical analyses are performed with the SPSS program package, version 10.0 (SPSS Inc., Chicago, Ill). Pearson $\chi^2$ tests and Student's t tests are used to compare the clinicopathologic characteristics of tumors (and patients) with high and low expression of CTGF. Survival is analyzed by the Kaplan-Meier method, and the log-rank test is used to test the difference in relapse time and survival between patients with tumors that have high and low expression of CTGF. The median survival times with 95% confidence intervals are calculated as described. Multivariable analyses with the Cox proportional hazards model are used to estimate the simultaneous effects of prognostic factors on survival. After confirmation that the data meet the assumptions for a proportional hazards analysis, the stepwise selection is used. Variables are retained in the model if the associated two-sided P values are 0.10 or less. All statistical tests are two-sided. P values of less than 0.05 are considered statistically significant.

As a result, RT-PCR shows that CTGF mRNA is highly expressed in CL1-0 cells that have low invasive and low metastatic ability, but is almost not detectable in highly invasive CL1-3 and CL1-5 cells (FIG. 1A, upper right panel). Boyden chamber assay shows that the invasive ability of CL1-3 and CL1-5 is fourfold to sixfold higher than that of CL1-0 cells (FIG. 1A, lower panel). The level of Cyr61 mRNA, another member of the CCN family, is the same in cell lines with low or high invasive ability (FIG. 1A, upper right). Western blotting reveals that CL1-0 cells express a high level of CTGF protein, and CL1-3 and CL1-5 cells express extremely low levels of CTGF protein (FIG. 1A, upper left panel); the level of Cyr61 protein appears constant in CL1-0, CL1-3, and CL1-5 cells (FIG. 1A, upper left panel). Other lung adenocarcinoma cell lines (A549, NICH520, and H928) are tested to determine whether this relationship between the level of CTGF and invasive ability is also present. A549 cells are more invasive than NICH520 and H928 cells (FIG. 1B, lower). The highly invasive A549 cells express a very low or non-detectable level of CTGF protein, whereas the less invasive NICH520 and H928 cells express high levels of CTGF protein (FIG. 1B, upper panel). Thus, expression of CTGF is inversely associated with an invasive and/or metastatic phenotype of lung adenocarcinoma cell lines.

EXAMPLE 2

Overexpression of CTGF Suppresses Invasion and Metastasis in vitro

To clarify the direct role of CTGF expression in the invasiveness of lung adenocarcinoma cells, human CTGF cDNA expression vectors or control vectors are transfected into the highly invasive CL1-5 cells. After G418 selection, two single clones (CL1-5/CTGF-3 and CL1-5/CTGF-10) are isolated, a clonal mixture (CL1-5/CTGF-M), and vector control clone (CL1-5/neo), and then the levels of CTGF expression are assessed in each.

Construction of CTGF/wt Expression Plasmids: Total RNA is extracted from CL1-0 cells, and CTGF cDNA is cloned and amplified by RT-PCR with the primers of SEQ ID NO: 6 and SEQ ID NO: 7 (PubMed serial number XM-037056), and subcloned into a pcDNA3/V5-His TOPO TA vector (Invitrogen, San Diego, Calif.). The CTGF-expressing vector CTGF/wt is used in transient and stable transfections of human lung adenocarcinoma cells in vitro.

Plasmid and Transient Transfection: The CTGF expression vectors are transiently transfected into CL1-5 and A549 cells with the TransFast™ transfection reagents (Promega, Madison, Wis., USA). Briefly, 3 μg of plasmid DNA (CTGF/wt) and 8 μg of transfection reagents are mixed, and the transfection protocol is carried out according to the manufacturer's instructions (Promega, Madison, Wis., USA). One hour after transfection, the cells are cultured in normal complete medium for another 8 hours. The transfected cells are harvested and subjected to an invasion assay and Western blot analysis.

Stable-Transfected Clone Selection: Purified plasmid DNA (3 μg) is transfected into CL1-5 and A549 cells with the TransFast™ transfection reagent (Promega, Madison, Wis., USA). Twenty-four hours after transfection, stable transfectants are selected in Gentamicin (G418; Life Technologies, Inc.) at a concentration of 600 μg/mL. Thereafter, the selection medium is replaced every 3 days. After 2 weeks of selection in G418, clones of resistant cells are isolated and allowed to proliferate in medium containing G418 at 100 μg/mL. Integration of transfected plasmid DNA is confirmed by RT-PCR and Western blot analysis.

In Vitro Cell Growth Assay: To rule out the possibility that the effect of CTGF on in vitro cell invasiveness caused by different proliferation rates among the cell lines, growth rates of CTGF-overexpressing cells and that of the corresponding vector control cells are compared. Control vector (pcDNA3), or the respective CTGF/wt expressing vector is added to 6-cm dishes initially containing $10^5$ cells per well. At regular intervals, cells are trypsinized and resuspended, and the cell numbers are counted by hemocytometer.

Figure 2:
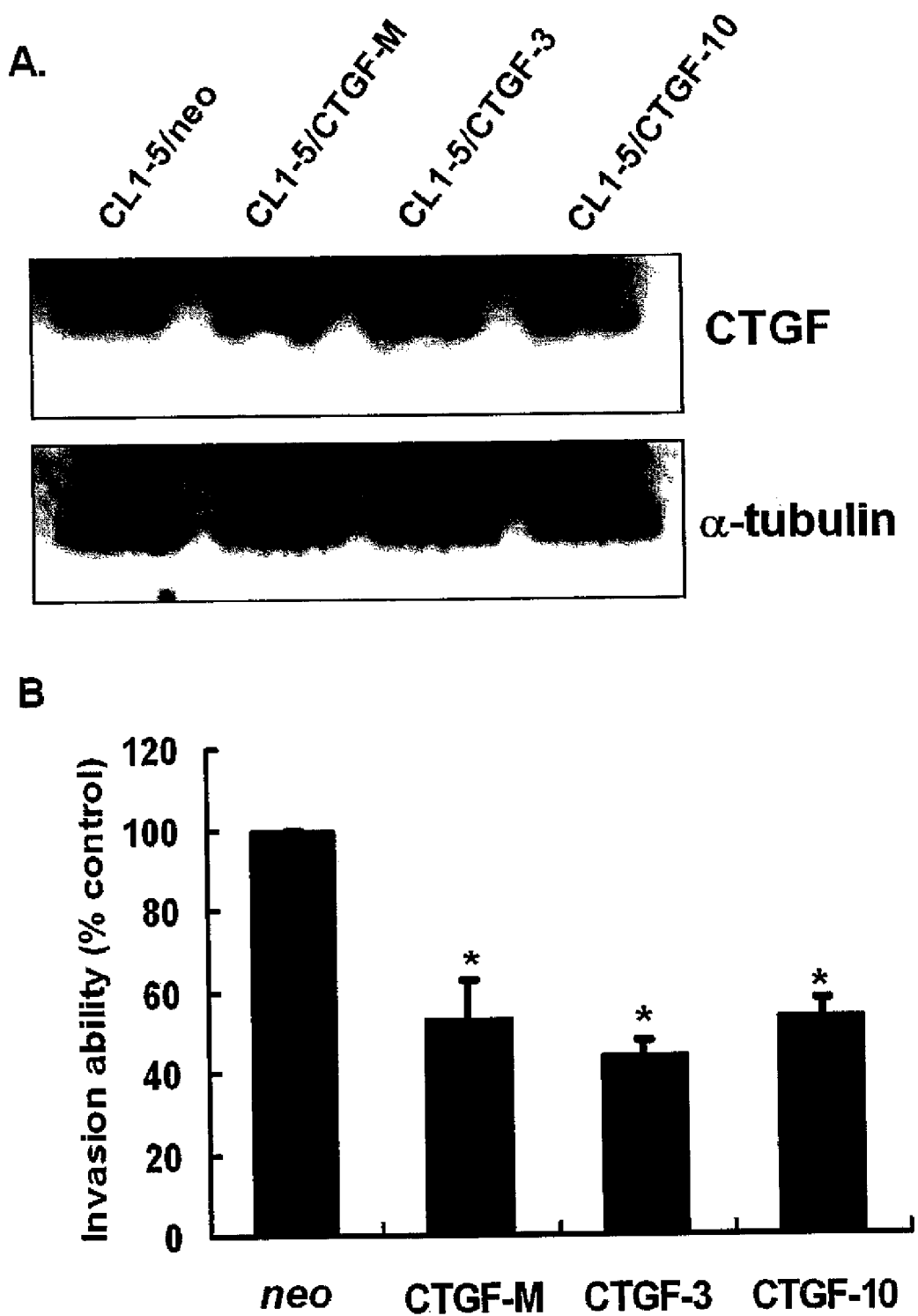
FIG. 2 shows overexpression of CTGF and suppression of invasion ability in transfected CL1-5 cells. A: Expression of CTGF protein in mock-transfected and CTGF-transfected CL1-5 clones assessed by immunoblot analysis to facilitate comparison of the relative CTGF protein expression between the mock-transfected clone CL1-5/neo and the CTGF-transfected clones CL1-5/CTGF-M, CTGF-3, and CTGF-10. B: In vitro invasion activity of CL1-5 cells stably transfected with CTGF or control vectors. In vitro invasion is measured in vitro with the Boyden chamber after 48 hours by determining the percentage of cells that migrate through Matrigel-coated filters in Transwell chambers (8-μm pore size). The invasive activity is statistically significantly lower in CTGF-transfected clones than CL1-5/neo vector control clone, as indicated by the asterisks (P=0.003, by a two-tailed Student's t test). Each clone is assayed in three experiments carried out in triplicate.
Figure 3:
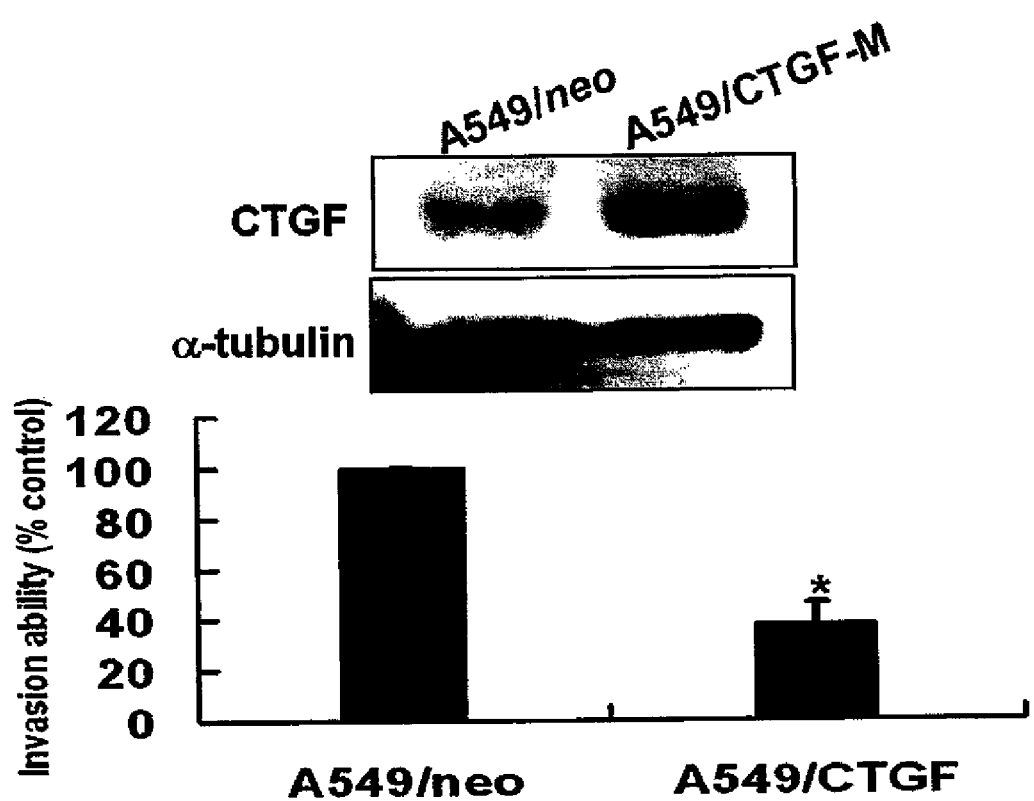
FIG. 3 shows overexpression of CTGF and suppression of invasion ability in transfected A549 cells. Upper panel: Immunoblot analysis of CTGF and α-tubulin expression in the mock-transfected A549 (A549/neo) cells, and CTGF-overexpressed mixture clone A549/CTGF-M. Lower panel: Expression of CTGF and the in vitro invasion activity of A549 cells stably transfected with CTGF or control vector. To compare the relative invasiveness between A549/neo and A549/CTGF-M cells, values are normalized to that of A549/neo cells. Error bars are the corresponding upper 95% confidence intervals. CTGF-transfected clones have statistically significantly lower invasive activity as shown by asterisks (P<0.001, by a two-tailed Student's t test) than A549/neo clones.

CTGF-overexpressing cell lines express 3.6-fold to 5.5-fold more CTGF protein than vector control cells (FIG. 2A). Invasive capacity is much lower in CTGF-transfected CL1-5 cells than in CL1-5/neo control cells (FIG. 2B) (percentage of invasive CL1-5/neo control cells: CL1-5/CTGF-M cells is 52.7% [95% CI is 23.9% to 70.8%], CL1-5/CTGF-3 cells is 44.0% [95% CI is 47.0% to 65.0%], and CL1-5/CTGF-10 cells is 54.0% [95% CI is 36.9% to 55.2%]; all P<0.001). Highly invasive A549 cells are also transfected with the CTGF expression vector or the control vector, and the invasive ability of the transfected cells is also examined. After transfection and selection in G418, a single clone (A549/CTGF) and a vector control clone (A549/neo) are isolated, and their expression of CTGF protein is assessed by Western blotting. CTGF-transfected A549 cells (A549/CTGF) clearly express CTGF protein (FIG. 3, upper), and the invasive ability of CTGF-overexpressing A549 cells is only about 40% of the control A549/neo cells (percentage of invasive A549/neo cells: A549/CTGF cells is 37.7% [95% CI is 37.0% to 87.7%]; P<0.001) (FIG. 3, lower).

Figure 4:
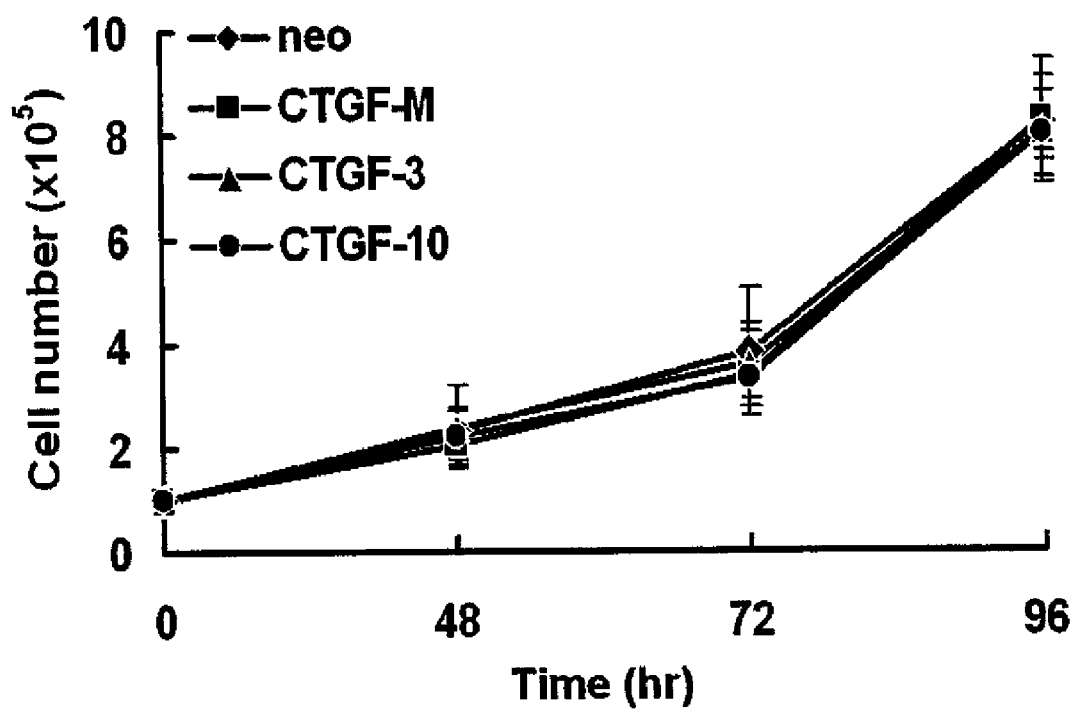
FIG. 4 shows growth properties of the vector (neo) and CTGF-transfected CL1-5 cells in monolayer culture cell lines. All experiments are carried out in triplicate on separate occasions with similar results. Error bars correspond to 95% confidence intervals.

The growth curves for the vector control cells CL1-5/neo and the CTGF-overexpressing cells CL1-5/CTGF-M, CL1-5/CTGF-3, and CL1-5/CTGF-10 are similar (FIG. 4), as are those for the vector control cells A549/neo and CTGF-overexpressing cells A549/CTGF-M (data not shown). Thus, the decreased invasiveness of these CTGF-transfected cells is apparently not caused by decreased proliferation rates.

EXAMPLE 3

Truncated CTGF Expression in Transfected CL1-5 Cells and Invasiveness of the Cells CTGF and other CCN proteins have a structure with several domains or modules. To determine which module participates in the inhibition of invasion, a series of CTGF deletion constructs are produced and characterized. Because CTGF is a secretory protein, the signal sequence at the amino-terminal end is retained and sequences at the carboxyl-terminal end are sequentially deleted.

Figure 5:
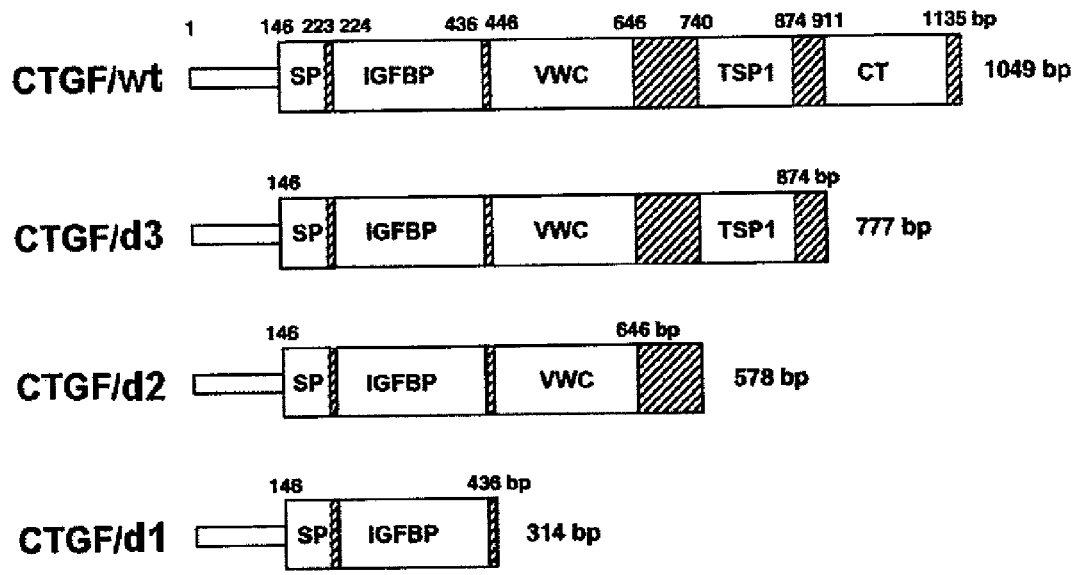
FIG. 5 shows truncated CTGF expression in transfected CL1-5 cells and invasiveness of the cells. A: Schematic representation of the CTGF full-length and truncated proteins expressed by the pcDNA3 plasmids. Numbers above the structural motifs indicate the nucleotide position of CTGF exon boundaries. IGFBP represents insulin-like growth factor binding protein; VWC represents Von Willebrand-type C motif; TSP1 represents thrombospondin type 1 motif; and CT represents carboxyl-terminal cysteine knots module. B: Invasive ability of CTGF deletion mutants. Serial deletion mutants are transiently transfected into CL1-5 cells and then seeded into Boyden chambers for 48 hours. Each clone is assayed in at least three experiments carried out in triplicate with similar results. *P<0.001 versus serial deletion mutants by using a two-tailed Student's t test.
Figure 5:
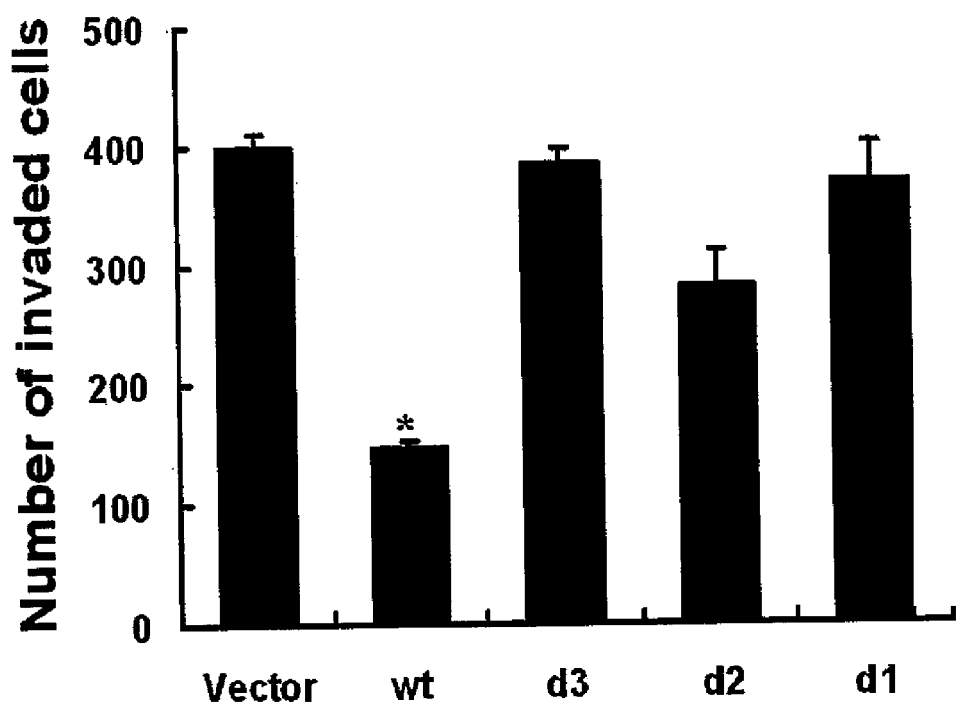

Construction of CTGF/wt Expression Plasmids and CTGF Deletion Mutants: The CTGF-expressing vector CTGF/wt is prepared according to the procedure in Example 2, and other three serial deletion mutants of CTGF are generated by deleting the CT domain (SEQ ID NO: 2); the CT and TSP-1 domains; or the CT, TSP-1, and VWC domains. These constructs are designated CTGF/d3, CTGF/d2, or CTGF/d1, respectively (FIG. 5A). Deletion constructs are generated with the reverse primer SEQ ID NO: 8 in combination with the forward primers SEQ ID NO: 9, SEQ ID NO: 10, and SEQ ID NO: 11, respectively. The products are subcloned into a pcDNA3 expression vector, and isolated clones are designated wt, d3, d2, and d1. The invasive capacities of transiently transfected CL1-5 cells expressing the full-length CTGF (CTGF/wt) or its deletion mutants CTGF/d3, CTGF/d2, or CTGF/d1 are determined according to described in Example 1.

Invasion assay shows that CL1-5 cells express CTGF/d3, which lacks the CT module, has a high invasive capacity that is equivalent to CL1-5 cells expressing the control vector (FIG. 5B). The mean number of invasive control CL1-5/neo cells and CL1-5 cells transfected with expressing plasmid CTGF/d3, a deletion of the CT module are 148 cells and 385 cells (difference is 237 cells, 95% CI is 208 to 266 cells; P<0.001), respectively. CL1-5 cells transiently transfected with CTGF/d2 or CTGF/d1 also have a relatively high invasive capacity compared with vector control cells.

EXAMPLE 4

Overexpression of CTGF Suppresses Invasion and Metastasis in vivo

Experimental Metastasis: Control vector- or CTGF-transfected tumor cells (CL1-5/CTGF-M or A549/CTGF-M) are prepared according to the procedures in Example 2, and cells are washed and resuspended in PBS. Subsequently, a single-cell suspension containing $10^6$ cells in 0.1 mL of PBS is injected into the lateral tail vein of 6-week-old male SCID mice (supplied by the animal center in the College of Medicine, National Taiwan University). Each clonal cell line is injected into 10 mice. The mice are killed after 8 weeks. (A preliminary study in this animal model indicates that CL1-5 cells develope numerous lung metastasis nodules by 8 weeks.) All organs are examined for metastasis formation. The lungs are removed, weighed, and fixed in 10% formalin. The number of lung tumor colonies is counted under a dissecting microscope. Representative lung tumors are removed, fixed, and embedded in paraffin. Embedded tissue is sectioned into 4-μm sections, and the sections are stained with hematoxylin and eosin for histologic analysis. All animal work is performed under protocols approved by the Institutional Animal Care and Use Committee (IACUC) of the College of Medicine, National Taiwan University.

Figure 6:
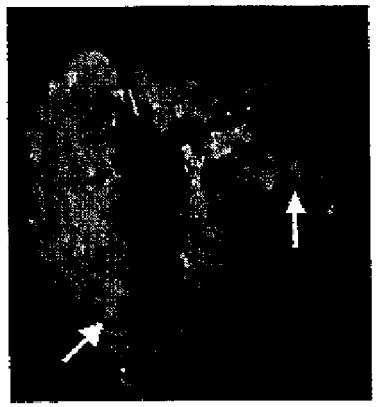
FIG. 6 shows suppression of human lung adenocarcinoma cell metastasis by CTGF in vivo. A: $10^6$ control vector- or CTGF-transfected tumor cells (CL1-5/CTGF-M or A549/CTGF-M) are suspended in 0.1 mL of PBS and injected into the lateral tail vein of SCID mice (10 mice per group). Animals are killed 2 months after intravenous injection, and lungs are excised and photographed after fixation. White arrows indicate metastatic tumor nodules. B: Histologic analysis of lung metastasis of CL1-5/neo control cells and CL1-5/CTGF-M cells. Lungs are embedded in paraffin, paraffin-embedded tissue is sectioned (4 μm thick), and sections are stained with hematoxylin-eosin. A metastatic tumor (T) is shown within the lung parachyma of a CL1-5/neo tumor (Left). The CL1-5/CTGF tumor (Right) has fewer foci.
Figure 6:
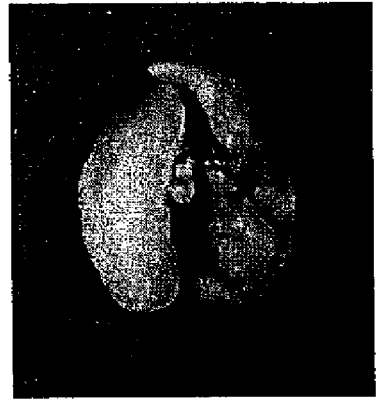
Figure 6:
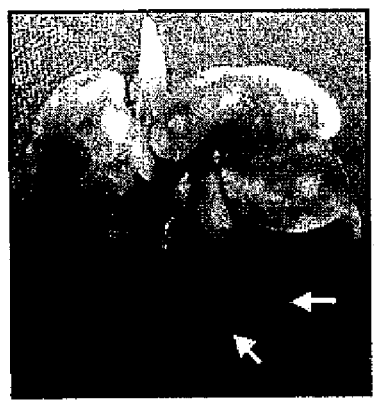
Figure 6:
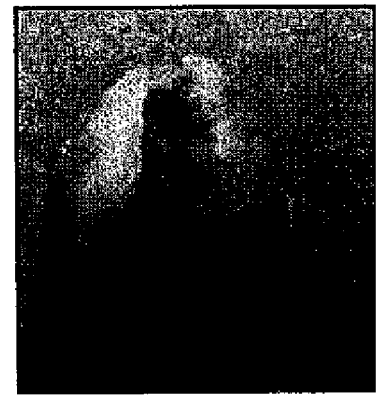
Figure 6:
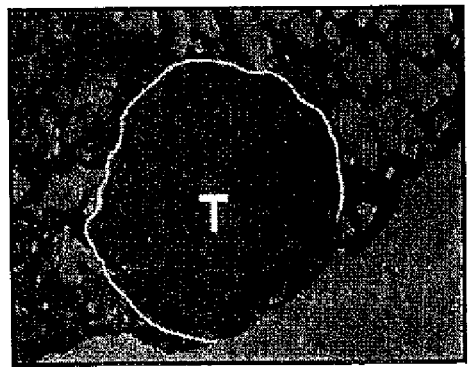
Figure 6:
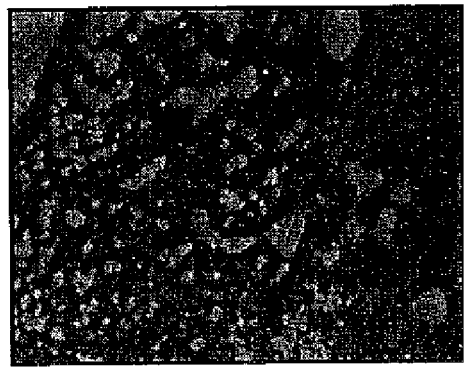

Results from FIG. 6A reveals that mice injected with CL1-5/neo or A549/neo control clones have numerous large lung metastases, whereas mice injected with CL1-5/CTGF-M or A549/CTGF-M cells have fewer and smaller metastatic nodules in the lung. Metastatic tumors formed in the lungs by CL1-5/neo cells have the morphology of a typical adenocarcinoma (FIG. 6B). Mice injected with CL1-5/neo cells have 77.5 metastatic lung nodules, and mice injected with CL1-5/CTGF-M have 12.3 metastatic lung nodules (difference is 65.2 nodules, 95% CI is 48.9 to 81.6 nodules; P<0.001). Mice injected with A549/neo have 61.3 metastatic lung nodules, and mice injected with A549/CTGF-M have 21.7 metastatic lung nodules (difference is 39.6 nodules, 95% CI is 23.4 to 56.0 nodules; P is 0.003). Thus, overexpression of CTGF in CL1-5 and A549 cells suppresses the ability of these cells to form metastatic nodules in the lungs.

The weight of lungs from mice injected with CL1-5/CTGF cells is 390 mg and that from mice injected with CL1-5/neo vector control cells is 448 mg (difference is 32 mg, 95% CI of the difference is 24 to 91 mg; P=0.005). The weight of lungs from mice injected with A549/CTGF cells is 473 mg and that from mice injected with A549/neo vector control cells is 617 mg (difference is 81 mg, 95% CI of the difference is 39 to 247; P=0.008). Thus, lung weight is decreased 13% in mice injected with CL1-5/CTGF cells and decreased 23.3% in mice given A549/CTGF cells, compared with lung weight in mice given vector control cells. Data from these two experiments are summarized in Table 1.

EXAMPLE 5

Association of CTGF Protein Expression with Lung Adenocarcinoma Tissue Stage, Tumor Status, Lymph Node Status, and Survival of Patients with Lung Cancer To investigate the involvement of CTGF in the progression of human lung adenocarcinoma, normal and tumor specimens from patients with lung adenocarcinoma are analyzed immunohistochemically for the expression of CTGF.

Patients and Specimens: Lung adenocarcinoma specimens are obtained from a total of 78 consecutive patients who undergo surgical resection at the National Taiwan University Hospital from Sep. 1, 1993, to Aug. 31, 1997. Patients who have previous history of cancers or have been treated with neoadjuvant chemotherapy and/or radiation therapy are not included from this study. Only lung adenocarcinoma specimens are included in this study. Paraffin-embedded, formalin-fixed surgical specimens are collected for immunohistochemical staining for CTGF. The group consists of 39 men and 39 women with an age of 62±11 years (mean±standard deviation). Written informed consent is obtained from all patients. The histologic identification of lung cancer is determined as recommended by the World Health Organization. Tumor size, local invasion, and lymph node metastasis are determined at pathologic examination. The final disease stage is determined by a combination of surgical and pathologic findings, according to the current tumor-node-metastasis system for lung cancer staging. Follow-up data are obtained from the patients' medical charts and from our tumor registry service. The survival time of patients is calculated from the date of operation to the date of death. The relapse time is calculated from the date of operation to the date of local recurrence or distant metastasis. Median follow-up is 37.4 months (ranging from 1 to 117 months).

Immunohistochemistry: After rehydration, sections (4 μm) of a paraffin-embedded tissue block that has been cut on glass slides are incubated in 3% hydrogen peroxide to block endogenous peroxidase activity. After trypsinization, the sections are blocked by incubation in 3% bovine serum albumin (BSA) in PBS. The primary antibody, a polyclonal goat anti-human CTGF antibody (R&D Systems, Minn.), are applied to the slides at a dilution of 1:50 and incubated at 4° C. overnight. After washes in PBS, the samples are treated with biotin-labeled secondary antibody (Santa Cruz Biotechnology, Santa Cruz, Calif.), at a dilution of 1:500 to 1:250 for 1 hour at room temperature. Detection is performed with an ABC-kit (DakoCytomation, Denmark). The slides are stained with diaminobenzidine (DAB), washed, counterstained with Delafield's hematoxylin, dehydrated, treated with xylene and mounted. A scoring system is devised to assign a staining intensity score for CTGF expression from 0 (no expression) to 3 (highest intensity staining). Immunostaining is classified into one of two groups according to both intensity and extent: low expression is defined as no staining present (staining intensity score=0) or positive staining detected in less than 10% of the cells (staining intensity score=1) and high expression is defined as positive immunostaining is present in 10% (staining intensity score=2) or more of the cells (staining intensity score=3).

Figure 7:
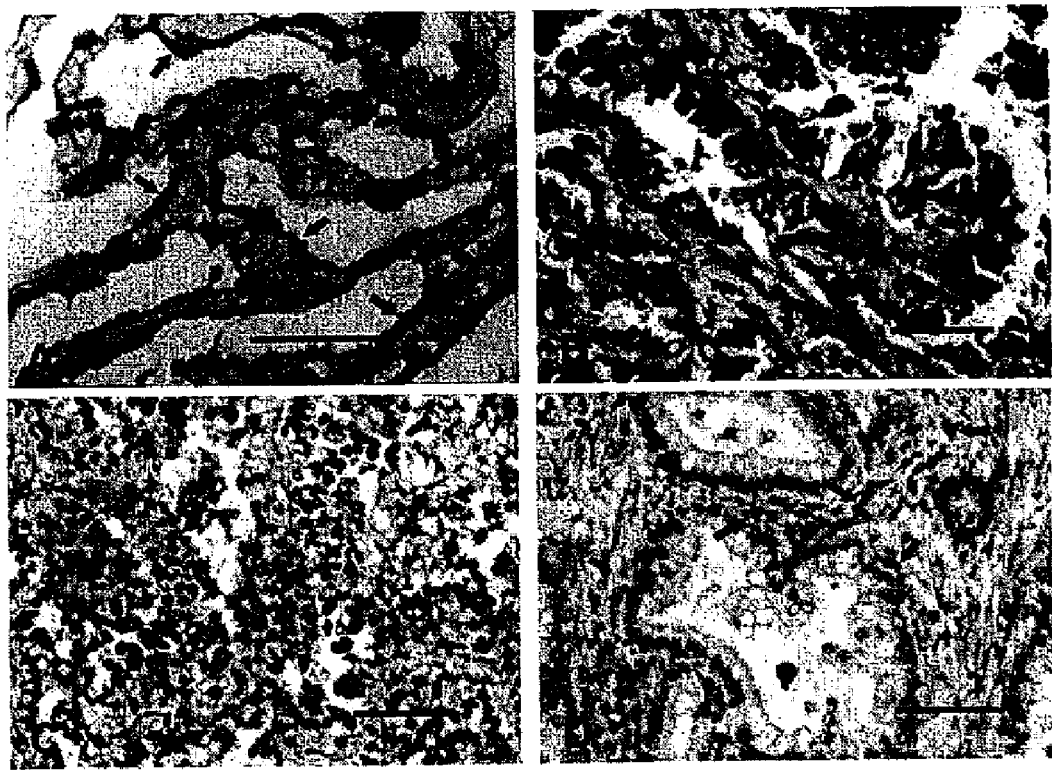
FIG. 7 shows immunohistochemistry of lung cancer tissue for CTGF expression. A: Representative staining of normal lung epithelium. The epithelial cells (black arrow) stain at intensity level 3 for CTGF. B: Representative section of lung adenocarcinoma (stage I). Carcinoma stains at intensity level 3 for CTGF. C: Representative section of a lung cancer metastasis to the brain (stage VI). The tumor part stains for CTGF at intensity level 1. D: Areas with carcinoma staining negative for CTGF are surrounded by areas of stromal cells staining at intensity levels 2 to 3 (black arrow). Scale bars represent 100 μm for A to D.

Expression of CTGF protein is high (intensity level 3) in the normal lung epithelium (FIG. 7A) and moderate to high (intensity level 2 to 3) in stage 1 lung adenocarcinoma cells (FIG. 7B). In these tumors, the protein is predominately localized to the cytoplasm. Expression of CTGF is reduced (intensity level 1) in low-grade metastatic epithelial tumor cells (FIG. 7C). CTGF is not detected in adenocarcinoma cells but is detected in the normal fibroblast and epithelial components of the same field, which are used as the corresponding positive staining control (FIG. 7D).

Figure 8:
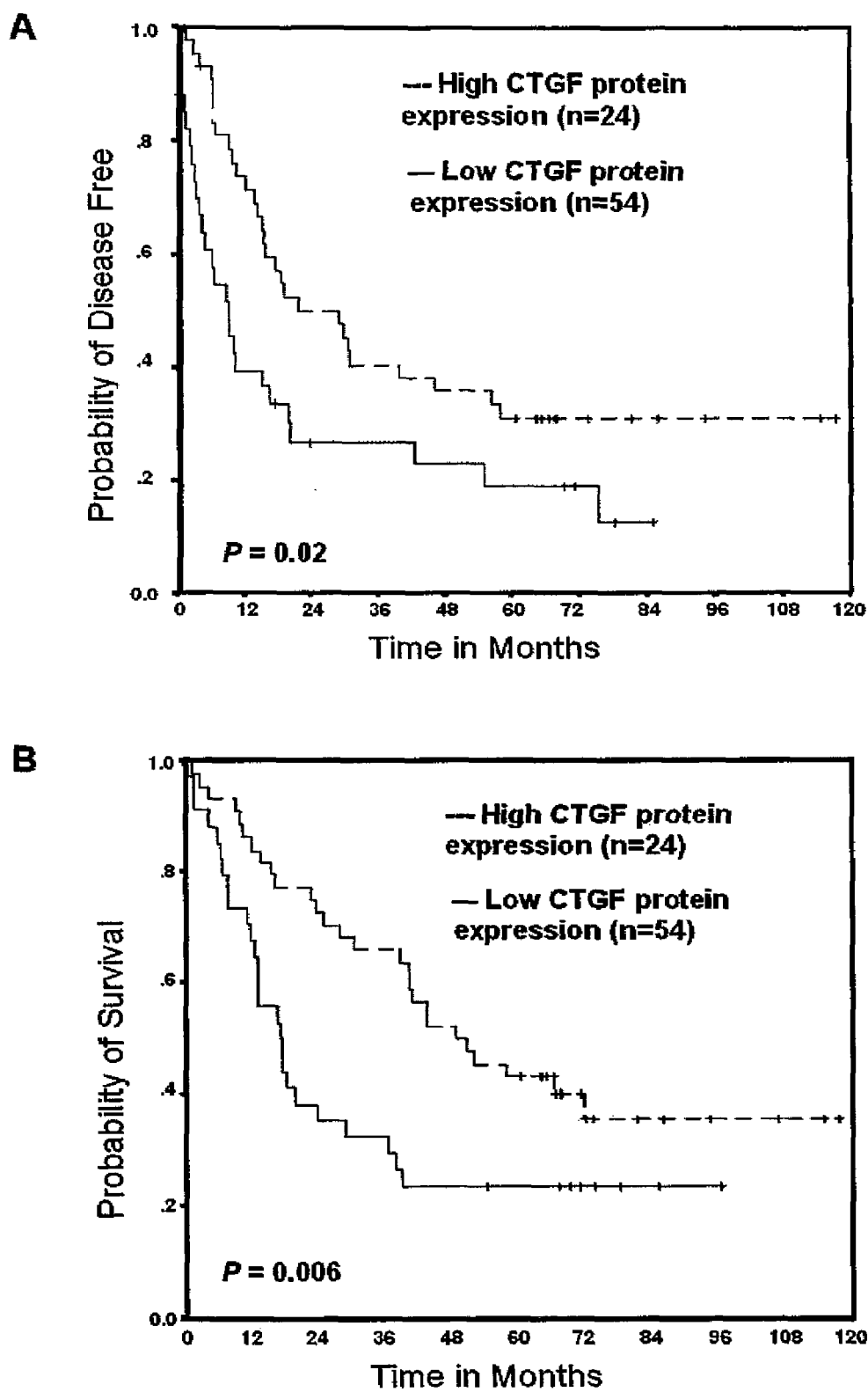
FIG. 8 shows Kaplan-Meier survival plots for patients with lung adenocarcinoma, grouped by the level of expression of CTGF protein. A: CTGF expression and disease-free survival. B: CTGF expression and overall survival. Overall survival is assessed in 78 patients with lung adenocarcinoma in relation to CTGF expression. Solid line represents patients with high expression (levels 3 and 2) of CTGF; dotted line represents patients with reduced or no expression of CTGF (levels 1 and 0). P value is determined by a two-sided log-rank test. The 20-month, 40-month, and 60-month disease-free survival rates are 52% (95% CI is 32% to 72%), 43% (95% CI is 23% to 64%), and 35% (95% CI is 15% to 54%), respectively, for patients whose tumors express high levels of CTGF, and 38% (95% CI is 25% to 52%), 30% (95% CI is 17% to 43%), and 22% (95% CI is 10% to 33%), respectively, for patients whose tumors express low levels of CTGF. The 20-month, 40-month, and 60-month overall survival rates are 87% (95% CI is 74% to 100%), 75% (95% CI is 58% to 92%), and 54% (95% CI is 34% to 74%), respectively, for patients whose tumors express high levels of CTGF, and 48% (95% CI is 35% to 61%), 33% (95% CI is 21% to 46%), and 26% (95% CI is 14% to 38%), respectively, for patients whose tumors express low levels of CTGF.

Table 2 also illustrates the level of CTGF protein associated with some prognostic factors for lung adenocarcinoma. The patients with lung adenocarcinoma are divided into two groups, those with tumors expressing low levels of CTGF (level 0 and 1) and those with tumors expressing high levels of CTGF (level 2 and 3). The low expression of CTGF is found to be statistically significantly associated with higher grade lymph node metastasis (N1-3 vs. N0, P=0.014), larger tumor size (T2-4 vs. T1, P=0.031), and advanced-stage disease (stage III-IV vs. stage I-II, P=0.001). The median time to postoperative disease recurrence is longer for patients whose tumors express a high level of CTGF (28.8 months; 95% CI is 8.0 to 49.6 months) than for patients whose tumors express a low level of CTGF (10.0 months; 95% CI is 3.3 to 16.7 months) (two sided log-rank test, P=0.07; FIG. 8A). The 5-year disease-free survival rate is 35% (95% CI is 15% to 54%) in the high expression group and 22% (95% CI is 10% to 33%) in the low expression group. In addition, the median survival time is longer for patients whose tumors express a high level of CTGF (66.7 months; 95% CI is 47.9 to 85.6 months) than for patients whose tumors express a lower level of CTGF (18.2 months; 95% CI is 5.2 to 31.1 months) (difference is 48.5 months, 95% CI is 33.5 to 63.5 months; two sided log-rank test, P=0.02, FIG. 8B). The 5-year overall survival rate is 54% (95% CI is 34% to 74%) in the high expression group and 26% (95% CI is 14% to 38%) in the low expression group. Thus, the expression of CTGF is statistically significantly associated with lymph node metastasis and overall survival.

EXAMPLE 6

Invasion Capacity of CRC Cell Lines is Inversely Related to CTGF Expression in vitro To explore whether CTGF affects the invasiveness of human CRC (colorectal cancer) cells, the expression level of CTGF in four human cancer cell lines, HCT116, COLO205, HT-29, and Caco-2, and a mouse cell line CT26 are examined by RT-PCR and Western blotting assay. Also, invasive ability of the cells is assayed by Boyden chamber assay.

Cell culture: HCT116 and Caco-2 cells are maintained in DMEM (Life Technologies, Inc.), with the addition of 4 mM L-glutamine and 10 mM sodium pyruvate (Sigma Chemical Co., St. Louis, Mo.). In addition, the medium used for Caco-2 cells is supplemented with 10 μg/ml transferrin. COLO205 and HT-29 cells are cultured in RPMI 1640 medium (Life Technologies), and the medium used for CT26 cells contains an additional 10 mM HEPES, 4.5 g/L glucose and 10 mM sodium pyruvate. All media used for cell culture are supplemented with 10% fetal bovine serum and a 1% penicillin (10,000 units/ml)-streptomycin (10,000 mg/ml) solution (Life Technologies, Inc.). Cells are maintained at 37° C. in the presence of 5% $CO_2$ in air. All cells are passaged into new medium every 2-3 days and before confluence.

Western blotting, RT-PCR, and Boyden chamber assay are performed according to what is described in Example 1.

Figure 9:
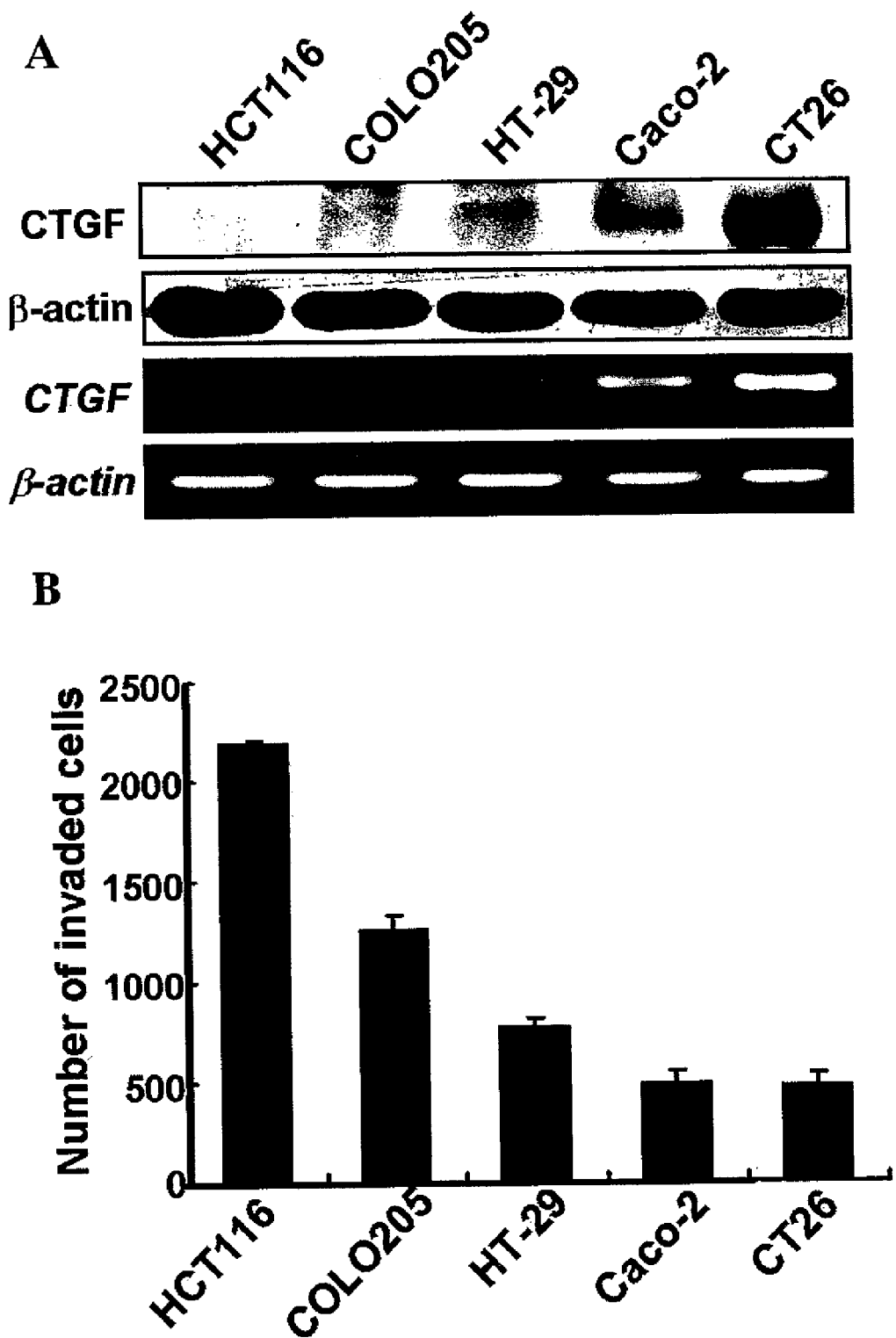
FIG. 9 shows CTGF expression and invasive ability of different colon cancer cell lines. A: Immunoblot analysis of CTGF and β-actin in human colon cancer cell lines. Protein extracts (40 µg/lane) from the indicated cell lines are electrophoresed, transferred, and used for immunodection of CTGF and β-actin (for an internal loading control) (upper). mRNA levels of CTGF and β-actin are measured semi-quantitatively by RT-PCR (lower). B: In vitro invasion assay performs in human colon cancer cell lines. Approximately $2.5 \times 10^4$ cells in 100 µL of complete medium are placed in the upper Boyden chamber with filter inserts (pore size, 8 µm) coated with Matrigel. After 48 hours in culture, cells are fixed in methanol and cells on the underside of the filters are viewed and counted. Each clone is plated in triplicate in each experiment.

Results from FIG. 9A show that HCT116 cells have the lowest mRNA (FIG. 9A, lower) and protein levels (FIG. 9A, upper) of CTGF. HT-29 and COLO205 cells exhibit moderate level of CTGF mRNA and protein. CT26 and Caco-2 cells have the strongest expression level of CTGF. Invasion assay of the cells reveals that HCT116 cells display the highest invasiveness among these cells; in contrast, Caco-2 and CT26 cells show only weak invasive ability (FIG. 9B). The above results demonstrate that invasive ability is inversely correlated with the level of CTGF expression in human CRC cell lines.

EXAMPLE 7

Altered Level of CTGF Affects the Invasiveness of Human CRC Cell Lines

To investigate the direct role of CTGF in the invasion and metastasis of human colorectal cancer, sense and antisense CTGF-expressing vectors are transfected into HCT116 and CT26 cells, respectively. After G418 selection, CTGF-overexpressing HCT116 (HCT116/CTGF), anti-sense CTGF-overexpressing CT26 (CT26/AS-CTGF) transfectants and Neo control cells are analyzed for their expression level of CTGF mRNA and protein.

Plasmid, Transient Transfection, and Reporter Gene Assay: The CTGF (sense) expression vectors are transiently transfected into HCT116 cells with TransFast™ transfection reagents (Promega, Madison, Wis., USA). Other procedures are as described in Example 2.

Generation of HCT116 and CT26 cell lines that constitutively express sense and antisense CTGF: HCT116 cells expressing CTGF (sense) or CT26 cells expressing CTGF (antisense) are established by transfection with the expression vectors, CTGF (sense) or CTGF (antisense). After 48 h of transfection, cells are trypsinized and replated in RPMI 1640 with 10% fetal calf serum and 1000 µg/ml G418. G418-resistant clones are selected and expanded.

Figure 10:
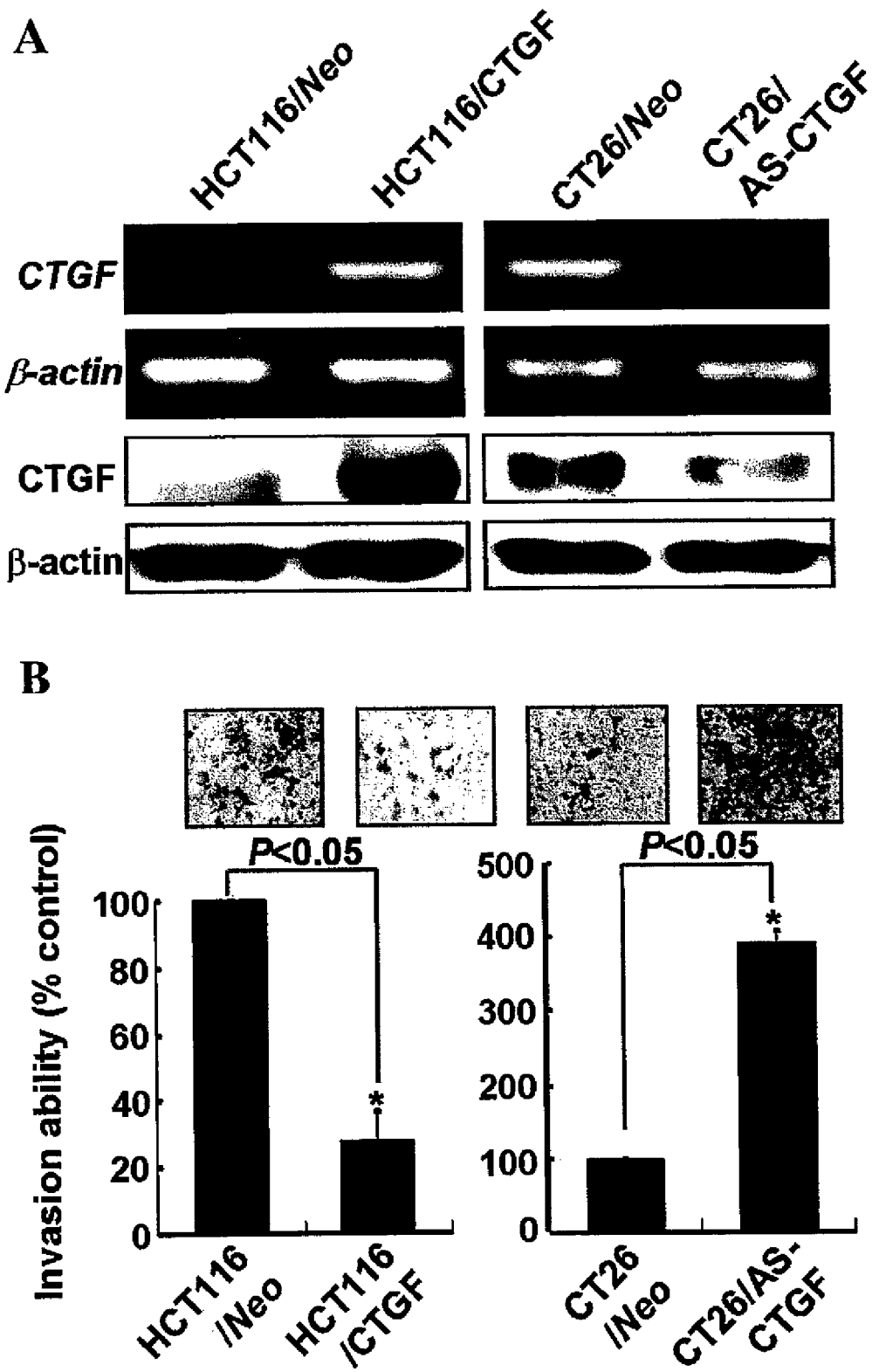
FIG. 10 shows CTGF expression in control vector (Neo) (HCT116/Neo, CT26/Neo), CTGF vector (HCT116/CTGF) and CTGF-antisense vector (CT26/AS-CTGF) transfected cells and the invasion abilities of these transfectants. A: mRNA levels of CTGF and β-actin as detected by RT-PCR (Upper). Western blot analysis of total cell lysates probed with antibodies to CTGF and β-actin (Lower). Stable clones are selected and obtained on 800 µg/ml G418. B: Invasion ability of HCT-116/Neo, HCT-116/CTGF (Left), and CT-26/Neo, CT26/AS-CTGF (Right). Upper micrographs show crystal violet staining of invading cells.

FIG. 10A shows that HCT116/CTGF cells exhibit a 4-5 fold increase of CTGF mRNA and protein as compared to HCT116/Neo cells. Interestingly, the invasive capacity of HCT116/CTGF cells is dramatically reduced to 20% of that of HCT116/Neo cells (FIG. 10B). Furthermore, the antisense CTGF transfection experiment shows that the endogenous CTGF mRNA and protein levels are effectively diminished in CT26/AS-CTGF cells (FIG. 10A). In a Boyden chamber assay, the invasive ability of CT26/AS-CTGF cells is increased about 3-4 fold over than that of CT26/Neo cells (FIG. 10B). This clearly shows that increased CTGF expression level in CRC cells result in inhibition of their invasive ability. To rule out the possibility that the effect of CTGF on in vitro cell invasiveness caused by different proliferation rates among these cell lines, growth rates of HCT116/CTGF, CT26/AS-CTGF, and their Neo control cells are compared. The growth rate of these cells is the same, suggesting that the altered invasive ability of those transfectants can not be attributed to their different growth rate (data not shown).

EXAMPLE 8

Reduced CTGF Expression in CT26 Cell Line Increases Liver Metastasis in vivo To further clarify whether modulation of CTGF expression affects the metastasis activity of colorectal cancer cells in vivo, BALB/c mice are given an intrasplenic/portal injection of CT26/AS-CTGF and CT26/Neo cells.

Experimental metastasis: CT26 cells or transfectants are washed, and $5 \times 10^5$ cells are suspended in 1 ml of PBS. Syngeneic 6-8 week-old BALB/c female mice are injected with 0.1 ml of these cells into the portal vein via intrasplenic injection, which is performed by a minilaparotomy (0.5 cm in length) over the left flank. Autopsies are performed when animals are moribund or after 6 weeks with macroscopic and microscopic examination for the presence of metastasis. These experiments are approved by the institute's Animal Welfare Committee.

Figure 11:
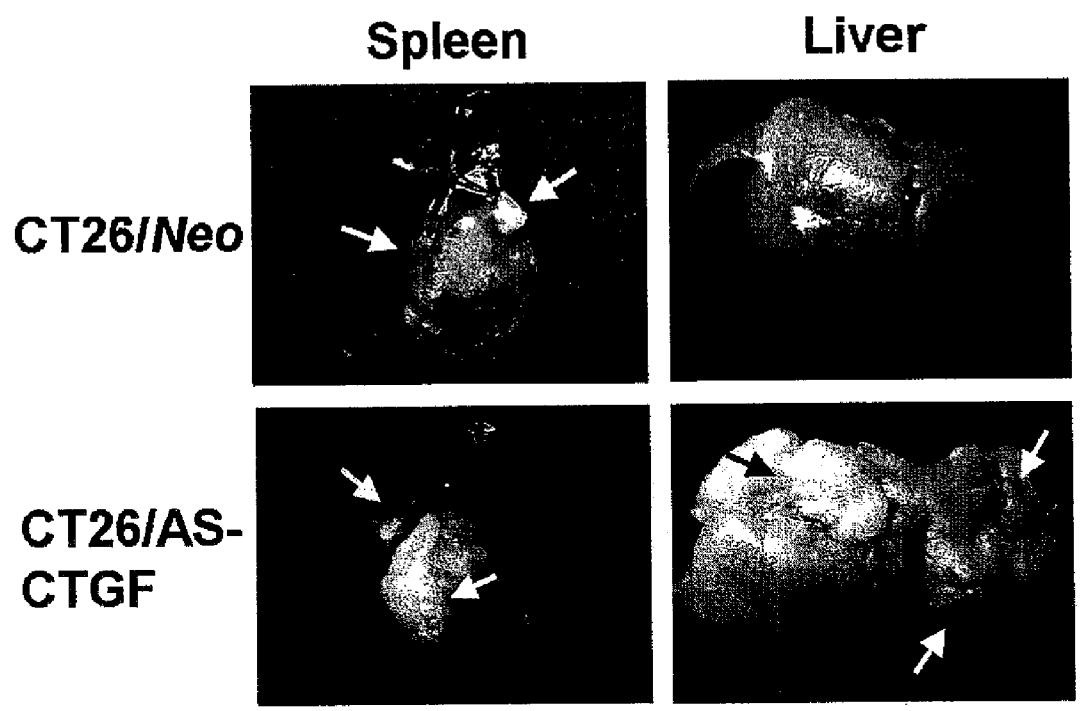
FIG. 11 shows liver metastasis of CT26/Neo and CT26/AS-CTGF transfectant cells. The photographs are spleens and livers from mice, which spleens are injected with either CT26/Neo or CT26/AS-CTGFcells; the livers and spleens are harvested when mice are moribund or after 6 weeks.
Figure 12:
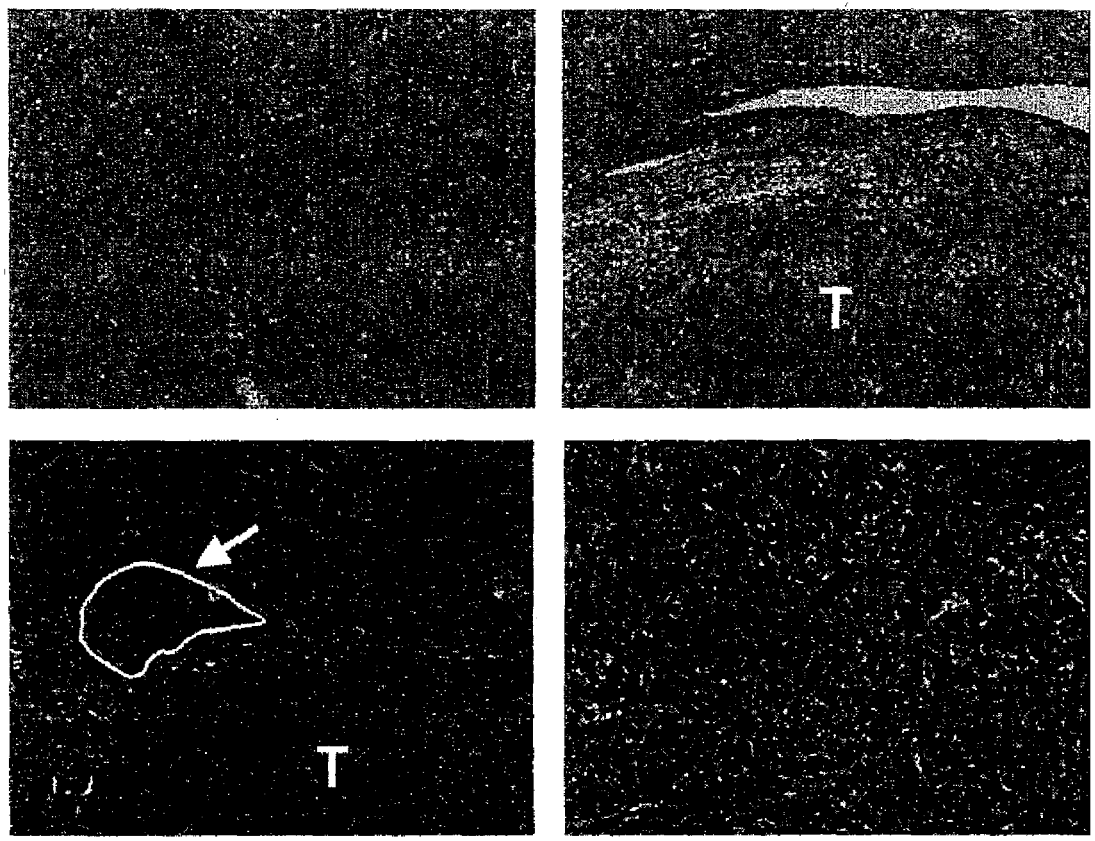
FIG. 12 shows histological analysis of liver metastasis of CT26/Neo cells and CT26-AS-CTGF cells, as indicated. Livers are embedded in paraffin and the paraffin-embedded tissue and sectioned (4 µm thick). The sections are stained with hematoxylin-eosin. Metastatic tumors (T) are shown within the liver parachyma. The CT26/Neo tumor (upper) shows fewer foci, and a smooth margin between the normal hepatocytes. The CT26/AS-CTGF tumor shows a satellite nodule (arrow) and an unsmooth, invaded border between the liver parachyma. The magnification factor of the CT26/AS-CTGF tumor is 100×.

Most mice injected with CT26/AS-CTGF cells become moribund within 4 weeks. CT26/AS-CTGF cells form intrasplenic tumors to the same extent and frequency as compared with CT26/Neo cells (FIG. 11). However, the number of hepatic metastatic nodules is significantly increased in mice injected with CT26/AS-CTGF as compared with CT26/Neo cells (FIG. 11, and Table 3; P=0.0039). The liver weight is also remarkably increased for those injected with CT26/AS-CTGF cells but not for those injected with the neo control cells (Table 3, P=0.0008). Histopathological examination of the metastatic tumors formed in the livers shows that CT26/AS-CTGF cells have an uneven invasive front, with vascular emboli (arrow) in the adjacent liver parachyma (FIG. 12, III and IV). In contrast, CT26/Neo cells have a smooth, pushing border (FIG. 12, I and II). The above results demonstrate that CTGF acts as a crucial negative regulator of hepatic metastasis by CRC in mice.

EXAMPLE 9

CTGF is an Independent Prognostic Factor in Patients with CRC

To investigate the involvement of CTGF in the progression, normal and tumor specimens are analyzed immunohistochemically for the expression of CTGF, and a CTGF-specific antibody is used to determine the expression level of CTGF in CRC. This antibody does not cross-react with other CCN members.

Patients: Our study includes 119 consecutive patients with CRC treated at National Taiwan University Hospital between December 1996 and July 1999. They are made up of 61 male and 58 female CRC patients. Their average age is 62.7±13.4 years (median 63, ranging 37-89 years). All patients undergo complete surgical resection, and their clinical and pathological data are available. Patients with familial adenomatous polyposis, hereditary non-polyposis CRC syndrome (according to Amsterdam criteria), inflammatory bowel diseases or who have had a malignant tumor within 5 years are excluded from this study. Tumor stage is based on the post-operative pathological report and a pre-operative clinical evaluation including chest radiogram, carcinoembryonic antigen (CEA) level and abdominal ultrasonography or computed tomography. Information about clinical outcome is obtained from a hospital chart review or a direct telephone interview with the patient's personal physician. All patients are followed up and this involved periodic examinations comprising serum blood-chemistry panels, CEA level, endoscopy and abdominal ultrasonography and radiograms of the thorax. Computed tomography or magnetic resonance imaging is also performed in cases where there is a suspected tumor recurrence. The overall survival time is calculated from the date of surgery to the time of the last visit or death and the disease-free survival time from the date of resection to relapse. The median follow-up time is 58.9 months. Tumor distribution according to primary site is 29 in right colon, 53 in the left colon (from splenic flexure to end of sigmoid colon) and 37 in the rectum. Fourteen patients have stage I, 37 have stage II, 51 have stage III and 17 have stage IV disease. The 5-year survival rates are 90%, 74.5%, 55.0% and 5.9% for stage I to IV, respectively.

Immunohistochemistry: All procedures are the same as described in Example 5 except samples are from normal colon epitheliums, colon polyp specimens, non-invasive colorectal tumors, and metastatic colorectal tumors. The results of immunohistological staining are classified using intensity; these are level 0 (negative staining), intensity level 1 (<5% of tumor cell stained), intensity level 2 (<50% of tumor cells stained), and intensity level 3 (>50% of tumor cells stained).

Figure 13:
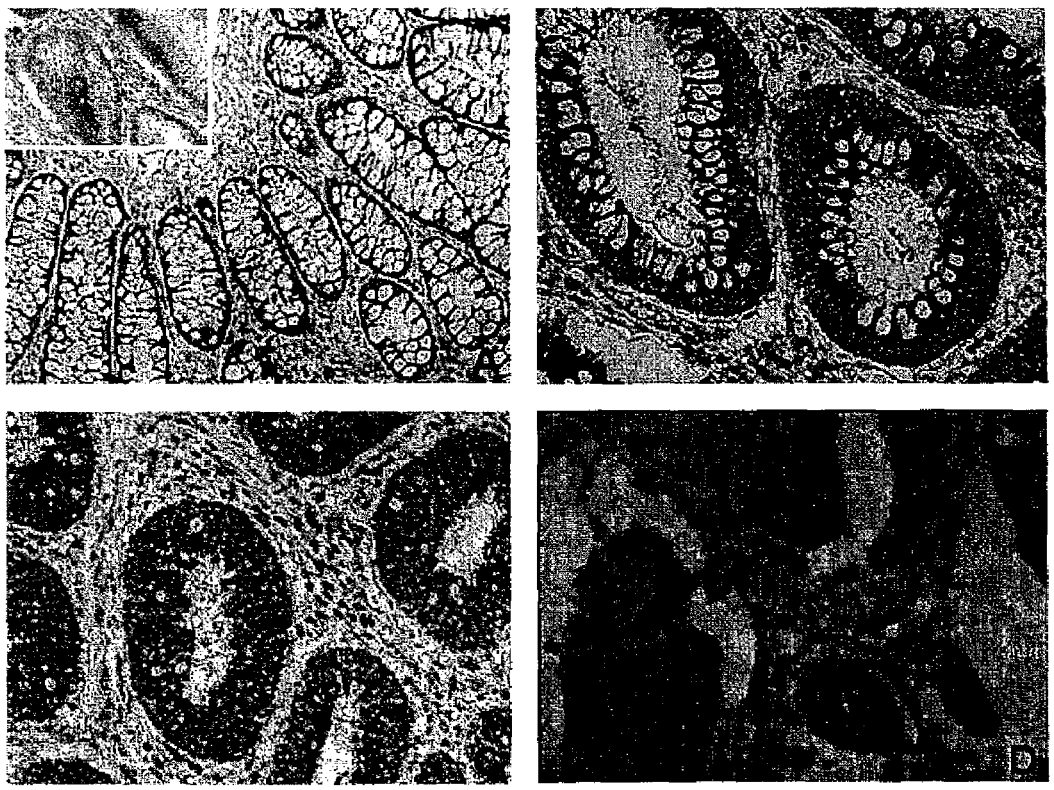
FIG. 13 shows representative CTGF immunohistochemical staining of normal human colon tissue, polyp, and colorectal carcinomas. High CTGF expression is shown in normal colon tissue (40× objective) (A) and colon polyp (B) (100×). The left upper insert in (A) shows negative control IgG staining of colon adenocarcinoma. High CTGF expression is found in moderate-differentiated adenocarcinoma tissue (C). CTGF is localized distinctly in the apical cytoplasm and membrane of the tumor cells. Low CTGF protein expression is noted in a poor-differentiated adenocarcinoma specimen (D).

The results of the immunohistological staining are classified as intensity level 0 (negative staining), intensity level 1 (<5% of tumor cell stained), intensity level 2 (<50% of tumor cells stained), and intensity level 3 (>50% of tumor cells stained). As shown in FIG. 13, high level of immunoreactivity for CTGF (intensity level 3) is detected in normal colon epithelium (FIG. 13A) and a colon polyp specimen (FIG. 13B). The CTGF protein is predominantly localized in the cytoplasm or the membrane of normal or tumor epithelial cells. Interestingly, highly differentiated and non-invasive colorectal tumors also show a high expression level for CTGF (FIG. 13C). In contrast, very weak immunoreactivity (intensity levels 0 and 1) for CTGF is observed in poor differentiated and metastatic colorectal tumors (FIG. 13D). Negative staining for CRC is showed when immunostaining using an IgG control (FIG. 13A, inset). Of the 119 CRC analyzed, low expression level (intensity levels 0 and 1) and high expression level (intensity levels 2 and 3) of CTGF in CRC specimens is 44% (53 of 119) and 56% (66 of 119), respectively. The incidence of low CTGF expression among the four TNM stages is 29% (4 of 14) in stage I, 35% (13 of 37) in stage 2, 47% (24 of 51) in stage III and 71% (12 of 17) in stage IV disease (P=0.059). The relationship between the level of CTGF expression and the clinicopathological characteristics are summarized in Table 3. No significant relationship is found between the level of CTGF expression and age of patients, their sex, tumor stage, tumor site, grade of differentiation, preoperative CEA level, and invasion depth. Colorectal tumors with low CTGF expression are more often detected as lymph node metastasis (P=0.044). Furthermore, CTGF expression is associated with disease outcome, that is, patients with low CTGF expression have the shorter survival (P<0.001) and more frequent recurrence (P<0.001) compared to CRC patients with high CTGF expression.

Figure 14:
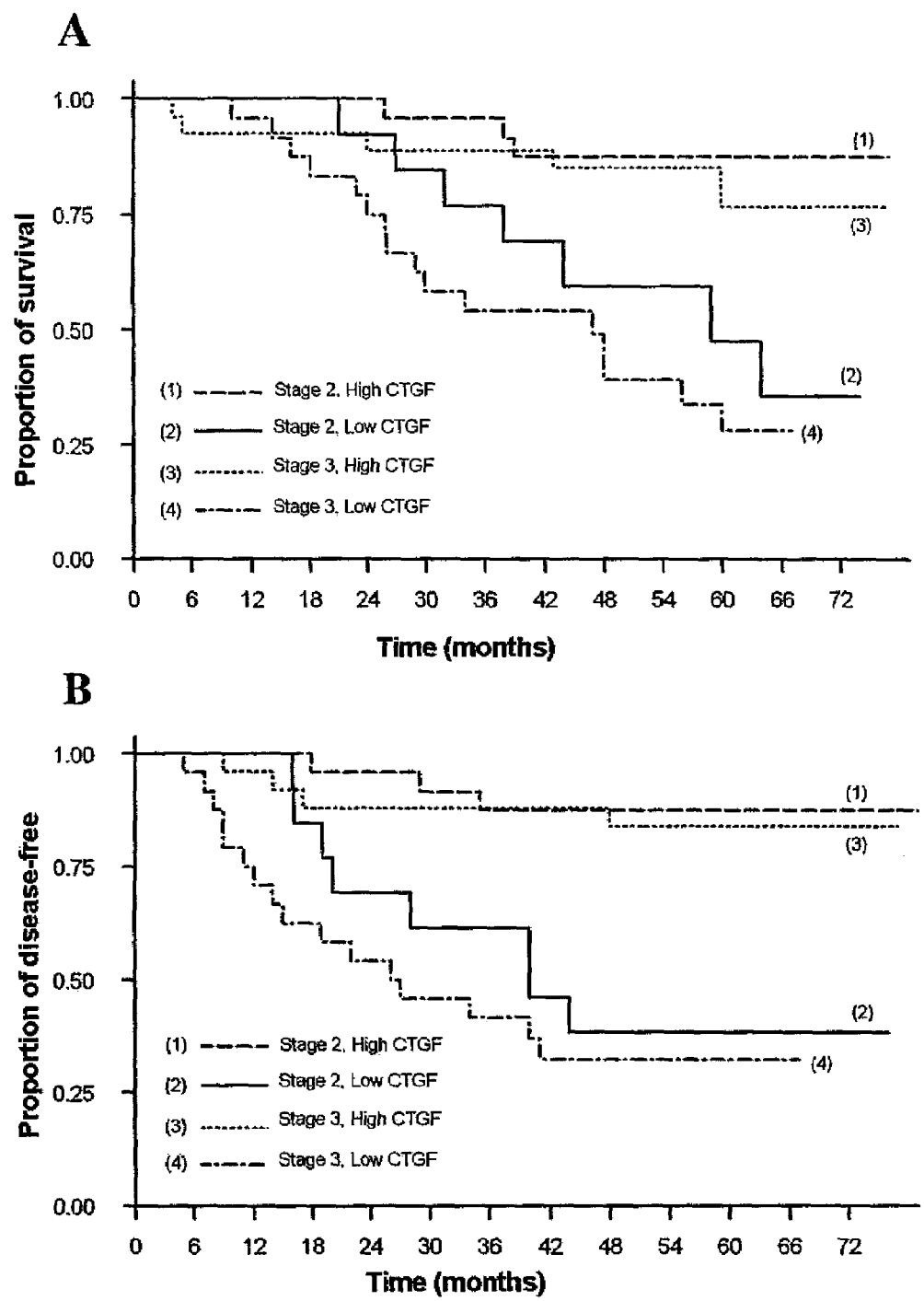
FIG. 14 shows univariate analysis of survival (Kaplan-Meier) considering stage II and III colorectal cancer patients. According to their CTGF expression of tumors, overall survival and disease-free survival of 119 patients are shown in (A) and (B), respectively.

Patients are stratified by tumor stage, stage II and III, and patients with high CTGF expression show a better survival rate and recurrent-free advantage compared to those with low CTGF expression (FIGS. 14A and B). Influence of each clinicopathological characteristic and the expression pattern of CTGF on patient survival and disease-free status of stage II and III patients is analyzed using the extended Cox regression model and the results are listed in Table 4. Among the stage 2 and 3 tumors, patients whose tumors have a high CTGF expression also have a better disease-free status (hazard ratio (HR)=0.143, P<0.001) and a better overall survival (HR=0.186, P<0.001) than those who have a low CTGF expression level. The data suggests that it is possible that invasion depth of T4 might increase the risk of recurrence (HR=3.72, P=0.04). CTGF expression is the most significantly independent predictor in this univariate model analysis and no other variables show a relationship to the disease outcome in the series of patients examined (Table 4). The 5-year survival rate for stage II disease patients with tumors showing higher CTGF expression is 87.5% but those with a lower CTGF expression is 47.5% (P=0.0052). In particular, the 5-year survival rate for stage III disease patients with tumors showing higher CTGF expression is 76.7% but those with a lower CTGF expression is only 28.1% (P=0.005). Similar results are obtained when the disease-free time is the end point, that is, patients whose tumors show a lower expression of CTGF, recurrence occurs earlier. Of the 51 patients with high CTGF expression in stage II and III CRC, only 7 (13.7%) develop tumor recurrence (6 distal metastasis and 1 loco-regional). In contrast, 24 of the 37 (64.9%) patients whose tumors have a low CTGF expression develop tumor recurrence (20 distal metastases and 4 loco-regional). A significant difference in 5-year survival between the patients with (77.9%) and without (8.0%) recurrence is noted (P<0.001). Taken together, all data strongly suggest that CTGF acts as an independent prognostic factor for CRC patients, especially for stages II and III tumors. Since the death of CRC patients is normally due to early metastasis, CTGF plays a role in modulating the invasiveness and metastasis of CRC.

TABLE 1

Antimetastatic effect of connective tissue growth factor (CTGF) in the lung metastasis model in SCID mice*

| | Lung metastasis | | | |
|---|---|---|---|---|
| | Nodule | | Weight | |
| Cell line | Median No. (range) | P value† | Median, mg (range) | P value† |
| CL1-5/neo | 77.5(69-91) | | 448(430-480) | |
| CL1-5/CTGF | 12.3(11-13) | <0.001† | 390(380-410) | <0.005† |
| A549/neo | 61.3(54-73) | | 617(600-640) | |
| A549/CTGF | 21.7(19-24) | 0.003† | 473(420-500) | 0.008† |

*Each group contains 20 moce. Statistical evaluation of the data is performed with a Student's t test. Test for simple comparison between two values is also used when appropriate. All statistical tests are two-sided.
†P values of less than 0.05 are considered statistically significant (CL1-5/neo versus CL1-5/CTFG; A549/neo versus A549/CTGF).

TABLE 2

Clinicopathologic characteristics of tumors with high and low expression of connective tissue growth factor (CTGF) protein

| | Low CTGF expression | High CTGF expression | P value |
|---|---|---|---|
| Characteristic | 54 | 24 | |
| Age, y (mean ± standard deviation) | 611.5 ± 11.0 | 62.0 ± 12.0 | 0.47* |
| Sex, No. of patients | | | |
| Male | 31 | 8 | 0.05 |
| Female | 23 | 16 | |
| Stage, No. of patients | | | |
| I and II | 19 | 18 | 0.001 |
| III and IV | 35 | 6 | |
| Tumor status, No. of patients | | | |
| T1 | 10 | 10 | 0.031 |
| T2-4 | 44 | 14 | |
| Lymph nodal status, No. of patients† | | | |
| N0 | 22 | 17 | 0.014 |
| N1-3 | 32 | 7 | |

*P value for age is derived with a two-sided Student's t test; other P values are derived with a two-sided Pearson chi-square test.
†The tumor stage, tumor status, and lymph node status are classified according to the international system for staging lung cancer.

TABLE 3

Clinical and pathological characteristics for high and low CTGF expression in colorectal cancer (CRC)

| Characteristics | | High-CTGF No. 66 | Low-CTGF No. 53 | P-value |
|---|---|---|---|---|
| Age (years, mean ± standard deviation) | | 61.7 ± 13.7 | 61.8 ± 13.0 | 0.889 |
| Sex | Male | 38 | 23 | 0.143 |
| | Female | 28 | 30 | |
| Tumor side[δ] | Right | 14 | 15 | 0.247 |
| | Left | 34 | 19 | |
| | Rectum | 18 | 19 | |
| Tumor differentiation | Poor | 4 | 3 | 0.158 |
| | Moderate | 58 | 40 | |
| | High | 4 | 9 | |
| CEA[$] level (ng/ml) | ≦3 | 33 | 25 | 0.854 |
| | >3 | 33 | 28 | |
| Stage | I | 10 | 4 | 0.059 |
| | II | 24 | 13 | |
| | III | 27 | 24 | |
| | IV | 5 | 12 | |
| Lymph node | 0 | 40 | 22 | 0.044* |
| | ≧1 | 26 | 31 | |
| Invasion depth | T1 | 1 | 3 | 0.278 |
| | T2 | 13 | 5 | |
| | T3 | 50 | 39 | |
| | T4 | 2 | 3 | |
| Intra-tumor invasion[Φ] | Present | 21 | 18 | 0.846 |
| | Absent | 45 | 35 | |
| Recurrence | No | 59 | 28 | <0.001* |
| | Yes | 7 | 25 | |
| Vital status | Alive | 53 | 17 | <0.001* |
| | Dead | 13 | 36 | |

*Statistical significance (P < 0.05).
[δ]Tumor side. Right: cecum to splenic flexture; Left: splenic flexture to sigmoid colon.
[$]CEA: carcinoembryonic antigen.
[Φ]Intra-tumor invasion (present): if pathologic report reveals one of venous, lymphovessel or perinurial invasions.

TABLE 4

Predictors[#] for mortality or recurrence in colorectal cancer of stage II or III

| | | Overall survival | | | Disease-free | | |
|---|---|---|---|---|---|---|---|
| Characteristic | Category | Hazard ratio | 95% CI | P value | Hazard ratio | 95% CI | P value |
| Sex | Male vs. Female (ref) | 1.39 | 0.7-2.8 | 0.36 | 1.34 | 0.6-2.7 | 0.42 |
| Age (years) | >65 vs. ≦65 (ref) | 1.66 | 0.5-5.1 | 0.37 | 1.41 | 0.5-4.3 | 0.54 |
| Tumor side | Right (ref) vs. left | 0.53 | 0.2-1.3 | 0.171 | 0.58 | 0.2-1.4 | 0.21 |
| | vs. rectum | 1.12 | 0.5-2.6 | 0.794 | 0.89 | 0.4-2.1 | 0.79 |
| CEA (ng/ml) | ≦3 (ref) vs. >3 | 1.02 | 0.5-2.1 | 0.96 | 1.10 | 0.5-2.2 | 0.80 |
| Tumor differentiation | Well (ref) vs. Moderate | 0.94 | 0.2-4.1 | 0.93 | 0.89 | 0.2-3.8 | 0.87 |
| | vs. Poor | 1.88 | 0.4-9.7 | 0.45 | 2.21 | 0.4-11.0 | 0.33 |
| Stage | II (ref) vs. III | 1.68 | 0.8-3.6 | 0.17 | 1.96 | 0.9-4.2 | 0.08 |
| Invasion depth | T2 (ref) vs. T3 vs. | 2.53 | 0.3-18.7 | 0.36 | 2.17 | 0.3-16.1 | 0.45 |
| | T4 (no T1) | 3.72 | 0.2-59.6 | 0.35 | 10.97 | 1.1-105.9 | 0.04* |
| Intratumor invasion | Present vs. Absent (ref) | 0.43 | 0.7-2.8 | 0.115 | 1.67 | 0.8-3.5 | 0.16 |
| CTGF expression | High vs. Low (ref) | 0.143 | 0.06-0.34 | <0.001* | 0.186 | 0.09-0.41 | <0.001* |

*Statistical significance (P < 0.05).
[#]Extended Cox regression model, univariate, with age as the time-varying covariate.

What is claimed is:

1. A method for determining metastatic potential of colorectal cancer cells, comprising the steps of evaluating expression levels of connective tissue growth factor (CTGF) in the cells, wherein the expression levels of CTGF in the colorectal cancer cells as compared to normal colon tissue cells is inversely associated with the metastatic potential of colorectal cancer cells, and the CTGF is encoded by a nucleotide of SEQ ID NO: 1.

2. The method according to claim 1, wherein the colorectal cancer cells express an expression levels of CTGF which is inversely associated with the metastatic potentials.

3. The method according to claim 1, wherein the steps comprise evaluating expressed protein levels of CTGF.

4. The method according to claim 1, wherein the steps comprises evaluating levels of mRNA encoding CTGF.

5. A method for determining metastatic potential of colorectal cancer cells, comprising the steps of evaluating expressed levels of CT module in a nucleotide sequence encoding connective tissue growth factor (CTGF) in the cells, wherein the expression levels of CTGF in the colorectal cancer cells as compared to normal colon tissue cells is inversely associated with the metastatic potential of the colorectal cancer cells, and the CT module is SEQ ID NO: 2.

6. The method according to claim 5, wherein the colorectal cancer cells express an expression levels of CTGF which is inversely associated with the metastatic potentials.

7. The method according to claim 5, wherein the steps comprise evaluating expressed protein or polypeptide levels of the CT module.

8. The method according to claim 5, wherein the steps comprise evaluating levels of mRNA encoding the CT module.

9. A method for determining metastatic potential of lung cancer cells, comprising the steps of evaluating expressed levels of CT module in a nucleotide sequence encoding connective tissue growth factor (CTGF) in the cells, wherein the expression levels of CTGF in the lung cancer cells as compared to normal lung tissue cells is inversely associated with the metastatic potential of the lung cancer cells, and the CT module is SEQ ID NO: 2.

10. The method according to claim 5, wherein the lung cancer cells express an expression levels of CTGF which is inversely associated with the metastatic potentials.

11. The method according to claim 5, wherein the steps comprise evaluating expressed protein or polypeptide levels of the CT module.

12. The method according to claim 5, wherein the steps comprise evaluating levels of mRNA encoding the CT module.

* * * * *

SEQUENCE LISTING

<160> NUMBER OF SEQ ID NOS: 11

<210> SEQ ID NO 1
<211> LENGTH: 2277
<212> TYPE: DNA
<213> ORGANISM: Human

<400> SEQUENCE: 1

| | | | | | |
|---|---|---|---|---|---|
| gacggcagcc | gccccggccg | acagccccga | gacgacagcc | cggcgcgtcc | cggtccccac | 60 |
| ctccgaccac | cgccagcgct | ccaggccccg | ccgctcccg | ctcgccgcca | ccgcgccctc | 120 |
| cgctccgccc | gcagtgccaa | ccatgaccgc | cgccagtatg | ggccccgtcc | gcgtcgcctt | 180 |
| cgtggtcctc | ctcgccctct | gcagccggcc | ggccgtcggc | cagaactgca | gcgggccgtg | 240 |
| ccggtgcccg | gacgagccgg | cgccgcgctg | cccggcgggc | gtgagcctcg | tgctggacgg | 300 |
| ctgcggctgc | tgccgcgtct | gcgccaagca | gctgggcgag | ctgtgcaccg | agcgcgaccc | 360 |
| atgcgacccg | cacaagggcc | tattctgtca | cttcggctcc | ccggccaacc | gcaagatcgg | 420 |
| cgtgtgcacc | gccaaagatg | tgctccctg | catcttcggt | ggtacggtgt | accgcagcgg | 480 |
| agagtccttc | cagagcagct | gcaagtacca | gtgcacgtgc | ctggacgggg | cggtgggctg | 540 |
| catgcccctg | tgcagcatgg | acgttcgtct | gcccagccct | gactgcccct | tcccgaggag | 600 |
| ggtcaagctg | cccgggaaat | gctgcgagga | gtgggtgtgt | gacgagccca | aggaccaaac | 660 |
| cgtggttggg | cctgccctcg | cggcttaccg | actggaagac | acgtttggcc | agacccaac | 720 |
| tatgattaga | gccaactgcc | tggtccagac | cacagagtgg | agcgcctgtt | ccaagacctg | 780 |
| tgggatgggc | atctccaccc | gggttaccaa | tgacaacgcc | tcctgcaggc | tagagaagca | 840 |
| gagccgcctg | tgcatggtca | ggccttgcga | agctgacctg | gaagagaaca | ttaagaaggg | 900 |
| caaaaagtgc | atccgtactc | ccaaaatctc | caagcctatc | aagtttgagc | tttctggctg | 960 |
| caccagcatg | aagacatacc | gagctaaatt | ctgtggagta | tgtaccgacg | gccgatgctg | 1020 |
| cacccccac | agaaccacca | ccctgccggt | ggagttcaag | tgccctgacg | gcaggtcat | 1080 |
| gaagaagaac | atgatgttca | tcaagacctg | tgcctgccat | acaactgtc | ccggagacaa | 1140 |
| tgacatcttt | gaatcgctgt | actacaggaa | gatgtacgga | gacatggcat | gaagccagag | 1200 |
| agtgagagac | attaactcat | tagactggaa | cttgaactga | ttcacatctc | attttccgt | 1260 |
| aaaaatgatt | tcagtagcac | aagttattta | aatctgtttt | tctaactggg | ggaaaagatt | 1320 |
| cccacccaat | tcaaaacatt | gtgccatgtc | aaacaaatag | tctatcaacc | ccagacactg | 1380 |
| gtttgaagaa | tgttaagact | tgacagtgga | actacattag | tacacagcac | cagaatgtat | 1440 |
| attaaggtgt | ggcttagga | gcagtgggag | ggtaccagca | gaaaggttag | tatcatcaga | 1500 |
| tagcatctta | tacgagtaat | atgcctgcta | tttgaagtgt | aattgagaag | gaaaatttta | 1560 |
| gcgtgctcac | tgacctgcct | gtagcccag | tgacagctag | gatgtgcatt | ctccagccat | 1620 |
| caagagactg | agtcaagttg | ttccttaagt | cagaacagca | gactcagctc | tgacattctg | 1680 |
| attcgaatga | cactgttcag | gaatcggaat | cctgtcgatt | agactggaca | gcttgtggca | 1740 |
| agtgaatttg | cctgtaacaa | gccagatttt | ttaaaattta | tattgtaaat | attgtgtgtg | 1800 |
| tgtgtgtgtg | tgtatatata | tatatatgta | cagttatcta | agttaattta | aagttgtttg | 1860 |
| tgccttttta | tttttgtttt | taatgctttg | atatttcaat | gttagcctca | atttctgaac | 1920 |
| accataggta | gaatgtaaag | cttgtctgat | cgttcaaagc | atgaaatgga | tacttatatg | 1980 |
| gaaattctgc | tcagatagaa | tgacagtccg | tcaaaacaga | ttgtttgcaa | agggaggca | 2040 |

```
tcagtgtcct tggcaggctg atttctaggt aggaaatgtg gtagcctcac ttttaatgaa    2100
caaatggcct ttattaaaaa ctgagtgact ctatatagct gatcagtttt ttcacctgga    2160
agcatttgtt tctactttga tatgactgtt tttcggacag tttatttgtt gagagtgtga    2220
ccaaaagtta catgtttgca cctttctagt tgaaaataaa gtgtatattt tttctat       2277

<210> SEQ ID NO 2
<211> LENGTH: 226
<212> TYPE: DNA
<213> ORGANISM: Human

<400> SEQUENCE: 2
gtgcatccgt actcccaaaa tctccaagcc tatcaagttt gagctttctg gctgcaccag     60
catgaagaca taccgagcta aattctgtgg agtatgtacc gacggccgat gctgcacccc    120
ccacagaacc accaccctgc cggtggagtt caagtgccct gacggcgagg tcatgaagaa    180
gaacatgatg ttcatcaaga cctgtgcctg ccattacaac tgtccc                   226

<210> SEQ ID NO 3
<211> LENGTH: 23
<212> TYPE: DNA
<213> ORGANISM: Artificial
<220> FEATURE:
<223> OTHER INFORMATION: CTGF primer

<400> SEQUENCE: 3
gcttaccgac tggaagacac gtt                                             23

<210> SEQ ID NO 4
<211> LENGTH: 22
<212> TYPE: DNA
<213> ORGANISM: Artificial
<220> FEATURE:
<223> OTHER INFORMATION: Cyr61 primer

<400> SEQUENCE: 4
cgaggtggag ttgacgagaa ac                                              22

<210> SEQ ID NO 5
<211> LENGTH: 20
<212> TYPE: DNA
<213> ORGANISM: Artificial
<220> FEATURE:
<223> OTHER INFORMATION: Actin primer

<400> SEQUENCE: 5
gatgatgata tcgccgcgct                                                 20

<210> SEQ ID NO 6
<211> LENGTH: 19
<212> TYPE: DNA
<213> ORGANISM: Artificial
<220> FEATURE:
<223> OTHER INFORMATION: Primer

<400> SEQUENCE: 6
atgaccgccg ccagtatgg                                                  19

<210> SEQ ID NO 7
<211> LENGTH: 24
<212> TYPE: DNA
<213> ORGANISM: Artificial
<220> FEATURE:
```

```
<223> OTHER INFORMATION: Primer

<400> SEQUENCE: 7
tcatgccatg tctccgtaca tctt                                          24

<210> SEQ ID NO 8
<211> LENGTH: 27
<212> TYPE: DNA
<213> ORGANISM: Artificial
<220> FEATURE:
<223> OTHER INFORMATION: Primer

<400> SEQUENCE: 8
cggaattcaa ccatgaccgc cgccagt                                       27

<210> SEQ ID NO 9
<211> LENGTH: 30
<212> TYPE: DNA
<213> ORGANISM: Artificial
<220> FEATURE:
<223> OTHER INFORMATION: Primer

<400> SEQUENCE: 9
gctctagatc agatgcactt tttgcccttc                                    30

<210> SEQ ID NO 10
<211> LENGTH: 30
<212> TYPE: DNA
<213> ORGANISM: Artificial
<220> FEATURE:
<223> OTHER INFORMATION: Primer

<400> SEQUENCE: 10
gctctagatc agtctgggcc aaacgtgtct                                    30

<210> SEQ ID NO 11
<211> LENGTH: 30
<212> TYPE: DNA
<213> ORGANISM: Artificial
<220> FEATURE:
<223> OTHER INFORMATION: Primer

<400> SEQUENCE: 11
gctctagatc agcagggagc accatctttg                                    30
```